(12) United States Patent
Mookerjee

(10) Patent No.: US 12,239,641 B2
(45) Date of Patent: Mar. 4, 2025

(54) METHODS OF TREATING OR PREVENTING FIBROSIS IN NON-ALCOHOLIC FATTY LIVER DISEASE

(71) Applicant: Rajeshwar Mookerjee, London (GB)

(72) Inventor: Rajeshwar Mookerjee, London (GB)

(*) Notice: Subject to any disclaimer, the term of this patent is extended or adjusted under 35 U.S.C. 154(b) by 1034 days.

(21) Appl. No.: 17/032,260

(22) Filed: Sep. 25, 2020

(65) Prior Publication Data

US 2021/0085668 A1    Mar. 25, 2021

Related U.S. Application Data

(63) Continuation of application No. PCT/GB2019/050879, filed on Mar. 27, 2019.

(30) Foreign Application Priority Data

Mar. 27, 2018  (GB) .................................... 1804922

(51) Int. Cl.
| | |
|---|---|
| *A61K 31/475* | (2006.01) |
| *A61K 31/4178* | (2006.01) |
| *A61P 1/16* | (2006.01) |
| *C12Q 1/6876* | (2018.01) |
| *G01N 33/50* | (2006.01) |

(52) U.S. Cl.
CPC ........ *A61K 31/475* (2013.01); *A61K 31/4178* (2013.01); *A61P 1/16* (2018.01); *C12Q 1/6876* (2013.01); *G01N 33/5067* (2013.01); *C12Q 2600/136* (2013.01); *C12Q 2600/158* (2013.01); *G01N 2333/726* (2013.01)

(58) Field of Classification Search
CPC .................................................. A61K 31/475
See application file for complete search history.

(56) References Cited

U.S. PATENT DOCUMENTS

| | | | |
|---|---|---|---|
| 5,503,978 A | | 4/1996 | Schneider et al. |
| 5,567,588 A | | 10/1996 | Gold et al. |
| 5,654,151 A | | 8/1997 | Allen et al. |
| 2007/0173505 A1* | | 7/2007 | Peng ..................... C07D 519/00 514/249 |
| 2009/0208550 A1* | | 8/2009 | Cronstein ............... A61K 31/52 514/263.34 |
| 2012/0220608 A1 | | 8/2012 | Belardinelli et al. |
| 2013/0237557 A1* | | 9/2013 | Mookerjee ......... A61K 31/4375 435/7.1 |

FOREIGN PATENT DOCUMENTS

| | | |
|---|---|---|
| CN | 102657868 A | 9/2012 |
| WO | 96/38579 A1 | 12/1996 |
| WO | 2012/020235 A1 | 2/2012 |
| WO | 2013/040316 A1 | 3/2013 |
| WO | 2015/143367 A2 | 9/2015 |
| WO | 2017/088974 A2 | 6/2017 |
| WO | 2018/174379 A1 | 9/2018 |

OTHER PUBLICATIONS

Chiang et al., Adenosine 2A Receptor Antagonist Prevented and Reversed Liver Fibrosis in a Mouse Model of Ethanol-Exacerbated Liver Fibrosis, PLoS One. 2013; 8(7): e69114 2013.*
Ebrahimi et al., New Concepts on Reversibility and Targeting of Liver Fibrosis; A Review Article, DOI: 10.15171/mejdd.2018.103, Middle East J Dig Dis/ vol. 10/ No. 3/ Jul. 2018.*
Sharma et al., Yohimbine ameliorates liver inflammation and fibrosis by regulating oxidative stress and Wnt/β-catenin pathway, Phytomedicine 123 (2024) 155182.*
Enomoto et al., Liver fibrosis markers of nonalcoholic steatohepatitis. World J. Gastroenterol. 2015; 21(24):7427-7435.
International Search Report issued in connection with corresponding International Application No. PCT/GB2019/050879, mailed Jul. 12, 2019, 2 pages.
Jones et al., THU-493—Treatment with the Adra2a antagonist, Yohimbine, reduces fibrosis progression and liver inflammation in a NASH fibrosis rat. Poster presentation from The International Liver Congress, 2018; J. Hepatol. 2018; 68:S352-S353.
Kleiner et al., Design and validation of a histological scoring system for nonalcoholic fatty liver disease. Hepatology 2005; 41:1313-21.
Le Corre et al., Biopharmaceutics and metabolism of yohimbine in humans. Eur. J. Pharm. Sci. 1999; 9:79-84.
Maddox et al., Elevated serum levels in human pregnancy of a molecule immunochemically similar to eosinophil granule major basic protein. J. Exp. Med. 1983; 158(4):1211-1226.
Sharma et al., Treatment with an alpha 2a adrenoreceptor antagonist modulates hepatic inflammation, markedly reduces portal pressure, and improves arterial pressure and hepatic blood flow in cirrhotic rats. Hepatology 2010; 52(Suppl. S1):1012A.
Singh et al., Fibrosis Progression in Nonalcoholic Fatty Liver versus Nonalcoholic Steatohepatitis: A Systematic Review and Meta-analysis of Paired-Biopsy Studies. Clin. Gastroenterol. Hepatol. 2015; 13:643-54.

* cited by examiner

*Primary Examiner* — Svetlana M Ivanova
(74) *Attorney, Agent, or Firm* — Kilpatrick Townsend & Stockton LLP

(57) ABSTRACT

The present invention derives from the unexpected finding that ADRA2a antagonists decrease fibrosis in non-alcoholic fatty liver disease (NAFLD). Thus, by antagonising ADRA2a, many of the unwanted consequences or symptoms of NAFLD, may be reduced, such as impaired cognitive activity and fibrosis progression. The present invention utilises these findings to identify and provide ADRA2a antagonists that may be used in the treatment of fibrosis in NAFLD.

10 Claims, 11 Drawing Sheets

A

B

A

B

A

Normal Chow     HFHC     HFHC + Yohimbine

A

B

METHODS OF TREATING OR PREVENTING FIBROSIS IN NON-ALCOHOLIC FATTY LIVER DISEASE

CROSS-REFERENCE TO RELATED APPLICATIONS

The present application is a continuation of International Application No. PCT/GB2019/050879, filed Mar. 27, 2019, which claims priority to United Kingdom Application No. GB1804922.1, filed Mar. 27, 2018, the disclosures of which are incorporated herein by reference in their entirety for all purposes.

FIELD OF THE INVENTION

The present invention derives from the unexpected finding that ADRA2a antagonists decrease fibrosis in non-alcoholic fatty liver disease (NAFLD).

Thus, by antagonising ADRA2a, many of the unwanted consequences or symptoms of NAFLD, may be reduced, such as impaired cognitive activity, non-alcoholic steatohepatitis (NASH) and fibrosis progression.

The present invention utilises these findings to identify and provide ADRA2a antagonists that may be used in the treatment or prevention of fibrosis and/or NASH in NAFLD.

BACKGROUND TO THE INVENTION

Liver disease represents the 5th most common cause of death for European citizens (45-65 yr olds). Alarming increases in obesity and diabetes coupled with changes in lifestyle and dietary habits, have contributed to a dramatic increase in rates of Non-alcoholic fatty liver disease (NAFLD) in 10-30% of the general population. If left untreated, NAFLD may progress through stages of increasing fibrosis, until the development of cirrhosis. NAFLD is fast becoming the commonest indication for liver transplantation in the UK and is associated with poor quality of life and a great health concern over the next decade. Treatment of NAFLD remains an unmet need. A key factor now recognised in NAFLD patients is impaired cognition, and this may affect up to 70% NAFLD cases with significant socio-economic impacts.

Whilst non-invasive diagnostic tests for NAFLD have increased, the management for those with fibrosis remains lifestyle related with no licensed therapies currently available. As such, up to 25% of patients with non-alcoholic steatohepatitis (NASH) (where inflammation compounds fatty liver) may progress over an average of 9 years to cirrhosis with consequent health-economic impact.

Fibrosis occurs in about one-third of NAFLD patients, and is the most important histological predictor of liver and non-liver related mortality. Fibrosis progression appears to parallel the emergence of diabetes in NAFLD patients and increasing body mass index. In NAFLD, whilst fibrosis tends to progress with time degree of histological fat decreases, often progressing to cirrhosis and an increased risk of decompensation and liver cancer. In more detail, NAFLD-NASH is a condition that is staged by histological progression, through grades of increasing inflammation (ballooning, presence of inflammatory foci within microscopic histological field), which can be measured through the well-known NAFLD activity score or "NAS" (see Kleiner, Brunt et al. (2005) Hepatology 41, 1313-21). In addition, this includes the progression of fibrosis as staged (i.e. fibrosis stage) by systems such as the Kleiner-Brunt scoring system as replicated below:

| Score | Feature |
|---|---|
| 0 | No Fibrosis |
| 1a | Zone 3 mild perisinusoidal fibrosis |
| 1b | Zone 3 moderate perisinusoidal fibrosis |
| 1c | Periportal/portal fibrosis only |
| 2 | Zone 3 and periportal/portal fibrosis |
| 3 | Bridging fibrosis |
| 4 | Cirrhosis |

This chart shows that in NAFLD, fibrosis progresses through stages 0, 1a-c, 2-3 and culminates in stage 4, with transition to cirrhosis. Whilst progression through to stage 3 is deemed entirely reversible and thereby targets for anti-fibrotic therapy (about 94% of NAFLD population), with transition to stage 4 and cirrhosis (5-6% NAFLD cases), the goal of management becomes decreasing risk of developing cirrhosis complications, clinically significant portal hypertension and hepatocellular cancer. The rate of progression of fibrosis stage is nearly twice in NASH vs. fatty liver alone (Singh S et al (2015) Clin Gastroenterol Hepatol 13, 643-54). This suggests treatments that also reduce hepatic inflammation (NASH) may have greater efficacy in decreasing fibrosis progression.

The available data shows the stage of fibrosis is directly related to increased risk of all causes of mortality, especially liver related deaths. In other words, once a patient has been identified to have fibrosis in NAFLD, their risk of liver disease progression and mortality goes up appreciably. There is therefore a need for treatments that decrease fibrosis early in NAFLD, and before irreversible progression to cirrhosis.

While some uses of antagonists of ADRA2a in the treatment of liver disease have been described in WO 2012/020235, this document only suggests that ADRA2a may be a target for the management of advanced cirrhosis. The management of cirrhosis, as highlighted above, is distinct from the treatment of early-stage fibrosis in NAFLD. Prior to the present invention, no link has been recognised between antagonists of ADRA2a and early-stage fibrosis in NAFLD. WO 2012/020235 contains no mechanistic reasoning for why any therapeutic compound which may help manage cirrhosis complications such as portal hypertension and systemic haemodynamics could also be useful in treating fibrosis and/or reversing NAFLD altogether.

SUMMARY OF THE INVENTION

Antagonizing the alpha 2A adrenoceptor (ADRA2A) provides a novel strategy for treatment of fibrosis in NAFLD as it addresses all the key factors in the pathogenesis and also many clinical consequence of the disease including: (i) decreases stellate cell activation and contractility (ii) decreases fibrogenic factors and inflammatory response which collectively may decrease fibrosis (iii) acts adjunctively with other medications to decrease insulin resistance (iv) has lipolytic activity especially in subcutaneous stores (v) improves cognitive function. It is also important that such a treatment does not aggravate issues such as obesity or aberrant lipid metabolism and storage in patients suffering from NALFD.

A drug currently available off prescription, Yohimbine, has cautions placed on its use in liver disease patients over numerous health portals. As such, the data of the present application, showing its efficacy in treating fibrosis in NAFLD is surprising, and would not be obvious to those familiar with Yohimbine, for use in this indication.

Accordingly, the invention provides an antagonist of alpha 2a adrenergic receptors (ADRA2a) for use in a method of treating an individual suffering from fibrosis in NAFLD. In other words, the present invention provides an antagonist of an alpha 2a adrenergic receptor (ADRA2a) for use in a method of treating an individual suffering from fibrosis in non-alcoholic fatty liver disease (NAFLD), or in preventing fibrosis in an individual suffering from NAFLD.

The individual may also be suffering from a variety of features associated with NAFLD, such as steatosis; steatohepatitis; metabolic syndrome; diabetes mellitus; cognitive dysfunction; functional impairment of daily living; increased plasma alanine and/or aspartate aminotransferases; and/or NASH.

In some embodiments, the individual may have a fibrosis stage of 0, 1a, 1b, 1c, 2 or 3, in accordance with the Kleiner-Brunt scoring system (as shown below).

| Score | Feature |
|---|---|
| 0 | No Fibrosis |
| 1a | Zone 3 mild perisinusoidal fibrosis |
| 1b | Zone 3 moderate perisinusoidal fibrosis |
| 1c | Periportal/portal fibrosis only |
| 2 | Zone 3 and periportal/portal fibrosis |
| 3 | Bridging fibrosis |
| 4 | Cirrhosis |

In the treatments as described herein for individuals suffering from NAFLD-NASH, the individual does not have a fibrosis stage of 4, in accordance with the Kelinear-Brunt scoring system. In other words, the individual does not have cirrhosis.

The ADRA2a antagonist may be used to prevent fibrosis in individuals suffering from NAFLD and/or in NASH. Such individuals may have a fibrosis stage of 0 in accordance with the Kleiner-Brunt scoring system.

The ADRA2a antagonist may be used to treat or prevent progression of fibrosis in NAFLD and in NASH.

The ADRA2a antagonist may be used to treat or prevent NASH.

The ADRA2a antagonist may lead to decreased expression of ADRA2a in the liver of the individual; and/or decreased levels of ADRA2a in the liver of the individual; and/or decreased ADRA2a activity such as signalling via ADRA2a in the liver of the individual. The antagonist may be (a) a specific antagonist of ADRA2a; (b) not an antagonist of ADRA2b; (c) not an antagonist of ADRA2c; (d) not an antagonist of ADRA1; (e) not an antagonist of ADRB; and/or (f) not activing via the serotonin antagonist pathways. The antagonist may be selected from BRL-44408, Yohimbine, Rauwolscine and other selective ADRA2A antagonists (e.g. BRL48962). In a preferred embodiment of the invention, the antagonist is Yohimbine.

Preferably, a treatment as described herein does not aggravate obesity and/or aberrant lipid metabolism and storage in the individual. Preferably, a treatment as described herein does not increase body weight and/or increase liver fat.

Thus, the present invention also relates to a method of treating or preventing fibrosis in NAFLD in an individual in need thereof, said method comprising a step of administering to said individual an antagonist of alpha 2a adrenergic receptor (ADRA2a). Similarly, the present invention also relates to the use of an ADRA2a antagonist in the manufacture of a medicament for use in the treatment of an individual suffering from fibrosis in NAFLD, or in preventing fibrosis in an individual suffering from NAFLD.

The invention also provides a method of identifying an agent suitable for use in treating fibrosis in NAFLD, the method comprising determining whether a test agent is capable of decreasing the amount of ADRA2a activity such as the amount of signalling via ADRA2a, wherein the ability to decrease the amount or such ADRA2a activity indicates that the compound may be suitable for use in treating fibrosis in NAFLD. Such a method may be carried out by assessing the amount of ADRA2a activity such as signalling via ADRA2a in cells or a tissue that expresses or contains ADRA2a. For example, the amount or activity of ADRA2a may be assessed in the liver or in tissue or cells derived from the liver, in the kidney, the gut or heart or cells derived from the kidney or heart; in inflammatory cells, platelets or neurons; or in another cell or tissue that expresses ADRA2a. Such a method may be carried out by administering a test agent to a rat model of NAFLD or NASH and determining whether the presence of the test agent leads to a decrease in the amount or activity of ADRA2a in the liver of the rat.

ADRA2a antagonism will also increase cAMP concentration in the cell and modulate calcium influx into cells. The concentration of both cAMP and calcium in the cell can be measured by techniques well known in the art. Thus in one embodiment, a method of identifying an agent suitable for use in treating fibrosis in NAFLD may comprise determining whether a test agent is capable of increasing the amount of cAMP and/or calcium ions inside cells.

DETAILED DESCRIPTION OF THE INVENTION

Figure 1:
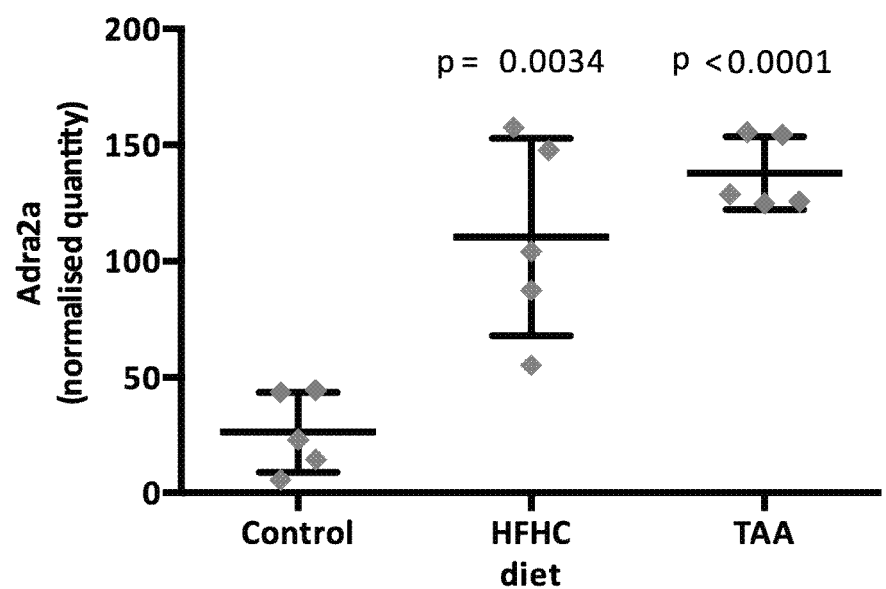
FIG. 1—Expression of ADRA2A receptors in liver tissue is up-regulated in a rat model of NASH induced by a high fat high cholesterol (HFHC) diet fed for 16 weeks compared to standard chow fed (control) animals. A further model inflammatory-fibrotic injury, thioacetamide (TAA) is also shown for comparison and also demonstrates ADRA2A up-regulation.

The sympathetic nervous system (SNS) is responsible for up- and down-regulating many homeostatic mechanisms in living organisms. Fibres from the SNS innervate tissues in almost every organ system, providing at least some regulatory function to things as diverse as pupil diameter, gut motility, and urinary output.

Noradrenaline (or norepinephrine) is a catecholamine with multiple roles including as a hormone and a neurotransmitter. Norepinephrine performs its actions on the target cell by binding to and activating adrenergic receptors. The target cell expression of different types of receptors determines the ultimate cellular effect, and thus norepinephrine has different actions on different cell types.

There are two main groups of adrenergic receptors, α and β, with several subtypes.
- α receptors have the subtypes $α_1$ (a $G_q$ coupled receptor) and $α_2$ (a $G_i$ coupled receptor).
- β receptors have the subtypes $β_1$, $β_2$ and $β_3$. All three are linked to G proteins (although 2 also couples to Gi).

Alpha-2-adrenergic receptors are members of the G protein-coupled receptor superfamily. They include 3 highly homologous subtypes: alpha 2a, alpha 2b, and alpha 2c. These receptors have a critical role in regulating neurotransmitter release from sympathetic nerves and from adrenergic neurons in the central nervous system. Studies in mouse revealed that both the alpha 2a and alpha 2c subtypes were required for normal presynaptic control of transmitter release from sympathetic nerves in the heart and from central noradrenergic neurons; the alpha 2a subtype inhibited transmitter release at high stimulation frequencies, whereas the alpha 2c subtype modulated neurotransmission at lower levels of nerve activity.

The alpha 1 adrenergic receptors are postsynaptic receptors couple with the $G_{αq}$ G-protein to stimulate phospholipase C and the $IP_3$-calcium pathway that promotes vasoconstriction. The alpha 2 adrenergic receptor couples with the $G_i$ G-protein with inhibitory effects on adenyl cyclase, they promote vasorelaxation and lower blood pressure.

$G_i$ alpha subunit (or $G_i/G_0$ or $G_i$ protein) is a heterotrimeric G protein subunit that inhibits the production of cAMP from ATP. This alpha subunit is the receptor of interest. It is located in Chromosome 7q21. $G_{αq}$ G-protein normally couples with alpha 1 adrenergic receptor. However there are many drugs like oxymetazoline which might act as an antagonist for alpha 1 receptor and antagonist for the alpha 2 adrenergic receptor.

The present invention lies in the finding that targeting of the alpha 2a adrenergic receptor has particular utility in patients suffering from fibrosis in NAFLD. Thus, by using an inhibitor of alpha 2a adrenergic receptor function, or an alpha 2a adrenergic receptor antagonist, symptoms associated with NAFLD such as cognitive impairment, steatosis, NASH and liver disease fibrosis progression can be reduced. The present invention can be used to prevent patients with NAFLD and/or non-alcoholic steatohepatitis (NASH) developing progression of fibrosis and would help to improve diabetic control in those NAFLD patients with co-associated diabetes mellitus; and reduce inflammation in those with NASH whilst also lowering liver fat and not increasing body weight.

ADRA2a Antagonists

The present invention relates to the antagonism of alpha 2a adrenergic receptors (ADRA2a). An antagonist of ADRA2a may be any compound or molecule that inhibits or decreases the activity, function or amount of ADRA2a. Preferably the antagonist functions in cells, tissues or organs that express ADRA2a such as in the liver of the patient. The antagonist may act preferentially in the liver or may act at a number of locations including the liver. The antagonist may act preferentially in particular cell types such as inflammatory cells, platelets or neurons. Preferably the antagonist leads to a decrease in ADRA2a activity, function or amount in the cells, tissues or organs of an individual to whom the antagonist is administered, such as in one of more of the liver, kidneys, brain, gut and the heart of the individual. The decrease in activity may be a decrease in signalling via ADRA2a. The antagonist may be targeted to the liver or other organs, cells or tissues such as those listed above during administration as discussed further below.

Preferred antagonists are those that decrease the activity (e.g. signalling via ADRA2a) or amount (e.g. expression level measured as mRNA or protein level) of ADRA2a by at least 10%, at least 20%, at least 30%, at least 40%, at least 50%, at least 60%, at least 70%, at least 80% or at least 90% compared to the amount seen in the absence of the antagonist. For example, decreases of these sizes may be seen in the liver or liver tissue of a subject to whom the agonist has been administered. Decreases of these sizes may be seen in other tissues or organs of the individual, such as in the kidney and/or heart of the individual.

An antagonist of ADRA2a may reduce the activity or amount of ADRA2a to an amount or activity that is the same, similar to, or equivalent to, that seen in an individual not suffering from fibrosis in NAFLD. For example, as explained herein, the expression of ADRA2a is found to be increased in association with a model of NAFLD. Use of an ADRA2a antagonist in accordance with the present invention may lead to a reduction in ADRA2a expression or activation downstream in the liver of the individual being treated to a normal level, such as a level that would be seen or would be expected in an individual not suffering from fibrosis in NAFLD.

The antagonist may act specifically or selectively to antagonise ADRA2a. The terms specific and selective are used interchangeably herein to refer to an effect in relation to ADRA2a in preference to an effect on other adrenergic receptors. That is, the effect of the antagonist on ADRA2a may be greater than any other biological effect of the antagonist. Such an antagonist may be specific to the inhibition of ADRA2a, that is it may decrease the activity of ADRA2a, but not other adrenergic receptors. By activity of ADRA2a herein is meant, for example, the signalling of ADRA2a. Such an antagonist may additionally or alternatively be specific to the expression of ADRA2a, that is it may decrease the expression of ADRA2a but not other adrenergic receptors.

A specific antagonist for use in accordance with the present invention may be an antagonist of ADRA2a as described herein, that does not act as an antagonist of other adrenergic receptor types such as ADRA2b, ADRA2c, ADRA1 and/or ADRB. A specific antagonist for use in accordance with the present invention may act on ADRA2a in preference to other adrenergic receptor types. For example, an antagonist of ADRA2a for use in accordance with the present invention may have one or more of the characteristics of an ADRA2a antagonist as described herein, such as this ability to reduce ADRA2a expression or signalling via ADRA2a, but may not have such characteristics in relation to other adrenergic receptor types, or may have such characteristics to a lower level in relation to other adrenergic receptor types when compared to ADRA2a.

For example, an antagonist that decreases the activity (e.g. signalling via that receptor) or expression of ADRA2a may not decrease the activity (e.g. signalling via that receptor) or expression of one or more other adrenergic receptor types, or may decrease the activity of the other adrenergic receptor type(s) to a lesser extent than for ADRA2a. The lesser extent may be measured as, for example, a lower percentage decrease when compared to the activity or expression in the absence of the antagonist, such as a decrease in activity or expression of less than 30%, less than 20%, less than 10%, less than 5%, less than 2%, less than 1% or less than 0.5% when compared to the activity or expression in the absence of the antagonist or when compared to its effect on ADRA2a. An antagonist that decreases the activity, expression or amount of ADRA2a may therefore not decrease the expression or amount of other adrenergic receptor types, or may decrease the expression of other adrenergic receptor types to a lesser extent, such as a lower percentage decrease, than its effect on ADRA2a.

Preferred selective or specific antagonists of the invention are those that may decrease the activity (e.g. signalling via ADRA2a) or amount (e.g. expression level measured as mRNA or protein level) of ADRA2a by at least 1.5 fold, at least 2 fold, at least 5 fold, at least 10 fold, at least 15 fold, at least 20 fold, at least 30 fold or greater, compared to the decrease in activity or amount of the other adrenergic receptor type.

Preferred selective or specific antagonists of the invention are those that have a selectivity for ADRA2a of at least 1.5 fold, at least 2 fold, at least 5 fold, at least 10 fold, at least 15 fold, at least 20 fold, at least 30 fold or greater, over their selectivity to other adrenergic receptor types.

Selective or specific antagonists of the invention may be selective for ADRA2 adrenoceptors over ADRA1 or ADRB adrenoceptors. In a preferred embodiment of the invention, the ADRA2a antagonist is not an antagonist of ADRA1 and/or is not an antagonist of ADRB. For example, Yohimbine and Rauwolscine have some affinity for all ADRA2a subtypes, but are most selective for ADRA2a. The affinity for Yohimbine is characteristic of ADRA2a.

Decreases in the expression of ADRA2a or other adrenergic receptor type can be measured by techniques known in the art, such as immunohistochemistry. Decreases in the activity of ADRA2a or other adrenergic receptor type can be measured by techniques known in the art, such as by measuring the output of the ADRA2a signalling pathway by measuring neurotransmitter release from sympathetic nerves or from adrenergic neurons. Measurements of expression or activity may be made, for example, using the techniques as shown in Example 2.

By other adrenergic receptor types herein is meant any adrenergic receptor that is not an alpha 2a adrenergic receptor. For example, the other adrenergic receptor type may be one or more of an alpha 2b adrenergic receptor (ADRA2b), an alpha 2c adrenergic receptor (ADRA2c), an alpha 1 adrenergic receptor (ADRA1), or a beta adrenergic receptor (ADRB) such as a beta1, beta2 or beta3 adrenergic receptor.

The other adrenergic receptor may be any one of these adrenergic receptor types. The ADRA2a antagonist may be specific to ADRA2a as discussed above in comparison to its effects on any other adrenergic receptor type. For example, the ADRA2a antagonist may be specific to ADRA2a in comparison to ADRA1.

The other adrenergic receptor may be more than one of these adrenergic receptor types. For example, the effects of the antagonist on an ADRA2a receptor may be specific, as discussed above, when compared to the effects of that agent on beta adrenergic receptors, when compared to the effects of that agent on alpha1 adrenergic receptors, and/or when compared to the effects of that agent when compared to other alpha 2 adrenergic receptors that are not alpha 2a adrenergic receptors such as alpha 2b and alpha 2c receptors. The effects of the antagonist on an ADRA2a receptor may be specific as discussed above when compared to all other classes of adrenergic receptor that are present.

The specificity of the ADRA2a antagonist may apply within the whole body of the individual to be treated, that is the actions of the ADRA2a antagonist may be specific as discussed above throughout the body of the individual. The specificity of the ADRA2a antagonist may apply within particular tissues of the individual, such as the liver, kidneys, brain, gut or heart. That is, in one embodiment, the ADRA2a antagonist may act specifically to antagonise ADRA2a as discussed above within the liver of the individual being treated.

The ADRA2a antagonist may therefore be a specific antagonist of ADRA2a as described above. For example, the ADRA2a antagonist may not be an antagonist of ADRA2b, or may have no significant effect on the activity (e.g. signalling) or expression of ADRA2b. The ADRA2a antagonist may not be an antagonist of ADRA2c or may not have any significant effect on the activity or expression of ADRA2c. The ADRA2a antagonist may not be an antagonist of ADRA1 (alpha 1 adrenergic receptor) or may not have any significant effect on the activity or expression of ADRA1. The ADRA2a antagonist may not be an antagonist of beta adrenergic receptors (ADRB) or may not have any significant effect on the expression or activity of ADRB.

Any agent capable of inhibiting the activity or function of ADRA2a may be suitable for use in the methods of the present invention. Antagonists for use in accordance with the present invention may be direct or indirect antagonists of ADRA2a.

Indirect antagonists are agents whose activity affect other members of the ADRA2a signalling pathway, thus indirectly inhibiting the activity or expression of ADRA2a.

Direct antagonists are agents whose activity is directly on ADRA2a. For example, direct antagonists may be agents that act directly on the ADRA2a receptor to decrease its activity. A direct antagonist may be an agent that disrupts ADRA2a function or that destabilises the ADRA2a receptor. A direct antagonist may decrease the amount of ADRA2a by destroying or disrupting ADRA2a molecules within the patient. A direct antagonist may be an agent that acts on the ADRA2a gene, promoter or other gene regulatory regions to decrease expression of the ADRA2a. A direct antagonist may decrease expression of ADRA2a by preventing or reducing expression from the endogenous ADRA2a gene.

Any agent or molecule having the properties described above may be used as an ADRA2a antagonist in accordance with the present invention.

Examples of ADRA2a antagonists or inhibitors that may be used in accordance with the present invention include:

BRL-44408

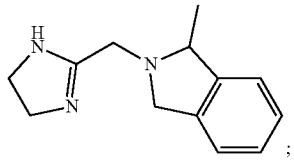

(2-[(4,5-Dihydro-1H-imidazol-2-yl)methyl]-2,3-dihydro-1-methyl-1H-isoindole), available from Sigma UK

BRL-48962

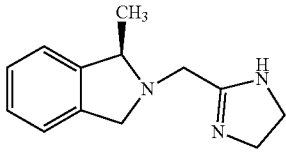

BRL 48962

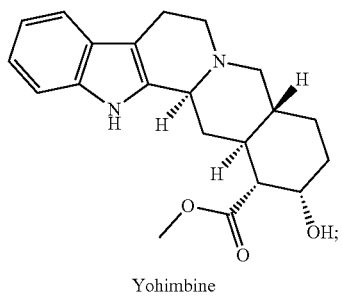

Yohimbine

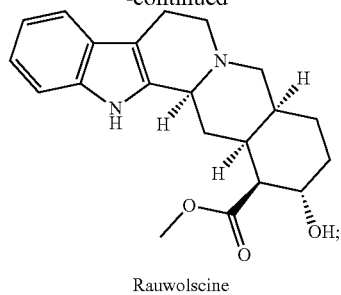

Rauwolscine

Selective antagonists of the invention include BRM 44408 and BRM 48962.

In a preferred embodiment of the invention, the ADRA2a antagonist is Yohimbine.

In some embodiments, the ADRA2a antagonist is a metabolite of Yohimbine, preferably a hydroxylated Yohimbine, preferably the 11-OH or the 10-OH derivatives, most preferably the 11-OH derivative. It has been shown that the 11-OH Yohimbine has a longer half life and better oral bioavailability than Yohimbine (Le Corre et al. (1999) Eur J Pharm Sci. 9, 79-84.).

The ADRA2a antagonist may be a molecule that is capable of binding to, and preventing or disrupting the activity of ADRA2a.

Accordingly, one group of ADRA2a antagonists for use in accordance with this invention are anti-ADRA2a antibodies. Such an antibody may be monoclonal or polyclonal or may be an antigen-binding fragment thereof. For example, an antigen-binding fragment may be or comprise a F(ab)2, Fab, scFv or Fv fragment, i.e. a fragment of the "variable" region of the antibody, which comprises the antigen binding site. An antibody or fragment thereof may be a single chain antibody, a chimeric antibody, a CDR grafted antibody or a humanised antibody.

An antibody may be directed to the ADRA2a molecule, i.e. it may bind to epitopes present on ADRA2a and thus bind selectively and/or specifically to ADRA2a. An antibody may be directed to another molecule that is involved in the expression and/or activity of ADRA2a. For example, a polyclonal antibody may be produced which has a broad spectrum effect against one or more epitopes on ADRA2a and/or one or more other molecules that are involved in the expression and/or activity of ADRA2a.

Antibodies can be produced by any suitable method. Means for preparing and characterising antibodies are well known in the art, see for example Harlow and Lane (1988) "Antibodies: A Laboratory Manual", Cold Spring Harbor Laboratory Press, Cold Spring Harbor, NY. For example, an antibody may be produced by raising antibody in a host animal against the whole polypeptide or a fragment thereof, for example an antigenic epitope thereof, herein after the "immunogen".

An antibody, or other compound, "specifically binds" to a molecule when it binds with preferential or high affinity to the molecule for which it is specific but does substantially bind not bind or binds with only low affinity to other molecules. A variety of protocols for competitive binding or immunoradiometric assays to determine the specific binding capability of an antibody are well known in the art (see for example Maddox et al, J. Exp. Med. 158, 1211-1226, 1993). Such immunoassays typically involve the formation of complexes between the specific protein and its antibody and the measurement of complex formation.

The ADRA2a antagonist may be an antisense oligonucleotide, such as an antisense oligonucleotide against the gene encoding an ADRA2a protein.

The term "antisense oligonucleotide" as used herein means a nucleotide sequence that is complementary to the mRNA for a desired gene. Such an antisense oligonucleotide may selectively hybridise with the desired gene. In the context of the present invention, the desired gene may be the gene encoding ADRA2a.

The ADRA2a antagonist may modulate expression of the ADRA2a gene. For example, the ADRA2a antagonist may be a short interfering nucleic acid (siRNA) molecule, double stranded RNA (dsRNA), micro RNA, deoxyribose nucleic acid interference (DNAi) or short hairpin RNA (shRNA) molecule.

The term "selectively hybridise" as used herein refers to the ability of a nucleic acid to bind detectably and specifically to a second nucleic acid. Oligonucleotides selectively hybridise to target nucleic acid strands under hybridisation and wash conditions that minimise appreciable amounts of detectable binding to non-specific nucleic acids. High stringency conditions can be used to achieve selective hybridisation conditions as known in the art. Typically, hybridisation and washing conditions are performed at high stringency according to conventional hybridisation procedures. Washing conditions are typically 1-3×SSC, 0.1-1% SDS, 50-70° C. with a change of wash solution after about 5-30 minutes.

The ADRA2a antagonist may be a nucleic acid molecule such as an antisense molecule or an aptamer. The nucleic acid molecule may bind a specific target molecule.

Aptamers can be engineered completely in vitro, are readily produced by chemical synthesis, possess desirable storage properties, and elicit little or no immunogenicity in therapeutic applications. These characteristics make them particularly useful in pharmaceutical and therapeutic utilities.

The terms "nucleic acid molecule" and "polynucleotide" are used interchangeably herein and refer to a polymeric form of nucleotides of any length, either deoxyribonucleotides or ribonucleotides, or analogs thereof. A nucleic acid may comprise conventional bases, sugar residues and internucleotide linkages, but may also comprise modified bases, modified sugar residues or modified linkages. A nucleic acid molecule may be single stranded or double stranded In general, aptamers may comprise oligonucleotides that are at least 5, at least 10 or at least 15 nucleotides in length. Aptamers may comprise sequences that are up to 40, up to 60 or up to 100 or more nucleotides in length. For example, aptamers may be from 5 to 100 nucleotides, from 10 to 40 nucleotides, or from 15 to 40 nucleotides in length. Where possible, aptamers of shorter length are preferred as these will often lead to less interference by other molecules or materials.

Aptamers may be generated using routine methods such as the Systematic Evolution of Ligands by EXonential enrichment (SELEX) procedure. SELEX is a method for the in vitro evolution of nucleic acid molecules with highly specific binding to target molecules. It is described in, for example, U.S. Pat. Nos. 5,654,151, 5,503,978, 5,567,588 and WO 96/38579. The SELEX method involves the selection of nucleic acid aptamers and in particular single stranded nucleic acids capable of binding to a desired target, from a collection of oligonucleotides. A collection of single-stranded nucleic acids (e.g., DNA, RNA, or variants thereof) is contacted with a target, under conditions favourable for binding, those nucleic acids which are bound to targets in the mixture are separated from those which do not bind, the nucleic acid-target complexes are dissociated, those nucleic acids which had bound to the target are amplified to yield a collection or library which is enriched in nucleic acids having the desired binding activity, and then this series of steps is repeated as necessary to produce a library of nucleic acids (aptamers) having specific binding affinity for the relevant target.

Any of the antagonists described herein may therefore be used to antagonise ADRA2a, i.e. to decrease the amount of ADRA2a that is present, and/or the activity (e.g. signalling via) or the function of the ADRA2a. This antagonism may take place in any location or tissue where ADRA2a is present. The antagonism may take place in one or more organs selected from the brain, kidney, liver and heart. The antagonism may take place on cells expressing ADRA2a, such as inflammatory cells, platelets and/or neurons. Preferably these antagonising effects take place in the liver.

An antagonist of ADRA2a may be an agent that decreases the production of endogenous ADRA2a. For example, the agent may act within the cells of the subject to inhibit or prevent the expression of ADRA2a. Such an agent may be a transcription factor or enhancer that acts on the ADRA2a gene to inhibit or prevent gene expression.

Screening Methods

The present invention also provides methods for the identification of agents suitable for use in the treatment of fibrosis in NAFLD. For example, the invention provides methods for the identification of antagonists of ADRA2a which are suitable for use in treating fibrosis in NAFLD. Antagonists identified by this method may be antagonists of ADRA2a having any of the characteristics or effects described above. Antagonists identified by the methods described herein may be suitable for use in the treatment of fibrosis in NAFLD or in the treatment or prevention of any of the conditions or symptoms described herein.

Accordingly, the invention provides a method of identifying an agent for use in the treatment of fibrosis in NAFLD, the method comprising determining whether a test agent is capable of decreasing the activity or expression of ADRA2a. For example, the method may involve determining whether a test agent is capable of decreasing the amount or activity of ADRA2a, wherein the ability to decrease the amount or activity of ADRA2a indicates that the compound may be suitable for use in treating fibrosis in NAFLD as described herein.

The method may comprise assessing the amount or activity of ADRA2a in a particular cell or tissue type. This may be any cell of tissue that expresses ADRA2a. For example, the method may assess the amount or activity of ADRA2a in the liver or in tissue or cells derived from the liver; in the kidney or heart or cells derived from the kidney or heart; in inflammatory cells, platelets or neurons; or in any other cell or tissue that expresses ADRA2a.

ADRA2a antagonism will also increase cAMP concentration in the cell and modulate calcium influx into cells. The concentration of both cAMP and calcium in the cell can be measured by techniques well known in the art. Thus in one embodiment, a method of identifying an agent suitable for use in treating fibrosis in NAFLD may comprise determining whether a test agent is capable of increasing the amount of cAMP and/or calcium ions inside cells.

A test agent for use in a screening method of the invention refers to any compound, molecule or agent that may potentially antagonise ADRA2a. The test agent may be, or may comprise, for example, a peptide, polypeptide, protein, polynucleotide, small molecule or other compound that may be designed through rational drug design starting from known antagonists of ADRA2a.

The test agent may be any agent having one or more characteristics of an antagonist of ADRA2a as described above.

The test agent to be screened could be derived or synthesised from chemical compositions or man-made compounds. Candidate agents may be obtained from a wide variety of sources including libraries of synthetic or natural compounds. Suitable test agents which can be tested in the above assays include compounds derived from combinatorial libraries, small molecule libraries and natural product libraries, such as display (e.g. phage display) libraries. Multiple test agents may be screened using a method of the invention in order to identify one or more agents having a suitable effect on ADRA2a, such as inhibition of ADRA2a activity or expression.

The screening methods of the invention may be carried out in vivo, ex vivo or in vitro. In particular, the step of contacting a test agent with ADRA2a or with a cell or tissue that comprises ADRA2a may be carried out in vivo, ex vivo or in vitro. The screening methods of the invention may be carried out in a cell-based or a cell-free system. For example, the screening method of the invention may comprise a step of contacting a cell or tissue comprising ADRA2a with a test agent and determining whether the presence of the test agent leads to a decrease in the amount or activity of ADRA2a in the cell or tissue.

For example, the ability of a test agent to decrease the activity or expression of ADRA2a may be tested in a host cell or tissue that expresses ADRA2a. For example, the amount or activity of ADRA2a may be assessed in vitro, in vivo or ex vivo in the liver or in tissue or cells derived from the liver, in tissue or cells from another organ that expresses ADRA2a, such as the kidney or heart, or in other cells that express ADRA2a such as inflammatory cells, platelets or neurons.

In such a cell-based assay, the ADRA2a and/or the test agent may be endogenous to the host cell or tissue, may be introduced into a host cell or tissue, may be introduced into the host cell or tissue by causing or allowing the expression of an expression construct or vector or may be introduced into the host cell or tissue by stimulating or activating expression from an endogenous gene in the cell.

In such a cell-based method, the amount of ADRA2a may be assessed in the presence or absence of a test agent in order to determine whether the agent is altering the amount of ADRA2a in the cell or tissue, such as through regulation of ADRA2a expression in the cell or tissue or through destabilisation of ADRA2a protein within the cell or tissue. The presence of a lower ADRA2a activity (e.g. a decreased amount of signalling via ADRA2a) or a decreased amount of ADRA2a within the cell or tissue in the presence of the test agent indicates that the test agent may be a suitable antagonist of ADRA2a for use in accordance with the present invention in the treatment of an individual having fibrosis in NAFLD.

In one embodiment, such a cell based assay may be carried out in vitro or ex vivo on cells or tissue deriving from the patient to be treated. It may therefore be determined whether or not the test agent is capable of decreasing the activity or amount of ADRA2a in the cells or tissue of that subject. For example, such a method may be carried out on a sample of cells or tissue from the liver of the patient.

A method of the invention may use a cell-free assay. For example, the ADRA2a may be present in a cell-free environment. A suitable cell-free assay may be carried out in a cell extract. For example, the contacting steps of the methods of the invention may be carried out in extracts obtained from cells that may express, produce or otherwise contain ADRA2a and/or a test agent. A cell-free system comprising ADRA2a may be incubated with the other components of the methods of the invention such a test agent.

In such a cell-free method, the amount of ADRA2a may be assessed in the presence or absence of a test agent in order to determine whether the agent is altering the amount of ADRA2a in the cell or tissue, such as through destabilisation of ADRA2a protein. In either case, the presence of a lower ADRA2a activity or a decreased amount of ADRA2a in the presence of the test agent indicates that the test agent may be a suitable antagonist of ADRA2a for use in accordance with the present invention in the treatment of an individual having fibrosis in NAFLD.

The contacting step(s) of the method of the invention may comprise incubation of the various components. Such incubations may be performed at any suitable temperature, typically between 4° C. and 40° C. Incubation periods may be selected for optimum activity, but may also be optimized to facilitate rapid high-throughput screening. Following the contact and optional incubation steps, the subject methods may further include a washing step to remove unbound components, where such a washing step is generally employed when required to remove label that would give rise to a background signal during detection, such as radioactive or fluorescently labelled non-specifically bound components.

Incubation in cell or cell-free assay systems may be performed in a microtiter plate (e.g. a 96-well plate or other microwell plate). Further, incubation may be performed in an automated fashion (e.g. for high-throughput screening).

A screening method of the invention may be carried out in vivo. For example, a screening method may be carried out in an animal model. The animal model may be model of NAFLD or NASH, such as high fat and high cholesterol fed rats. In such an in vivo model, the effects of a test agent may be assessed in the liver, or in other organs, cells or tissues that express ADRA2a such as the kidney, gut or heart or in inflammatory cells, platelets or neurons. Preferably, the animal is a non-human animal such as a rat.

For reference, carbon tetrachloride ($CCl_4$), thioacetamide (TAA), dimethylnitrosamine (DMN), and diethylnitrosamine (DEN) are the most commonly used toxic agents to induce liver fibrosis in rodents.

Accordingly, the screening method of the present invention may comprise the step of administering a test agent to a rat model of NAFLD or NASH and determining whether the presence of the test agent leads to a decrease in the amount or activity of ADRA2a in the liver or other organs, cells or tissues of the rat as discussed above.

Such a model may be used to assess the in vivo effects of a test agent. For example, such a model may be used to assess whether the test agent is capable of decreasing the activity or amount of ADRA2a in vivo. In such a method, the amount of ADRA2a may be assessed and/or the activity of ADRA2a, such as signalling by ADRA2a, may be assessed.

An in vivo model may also be used to determine whether the test agent has any unwanted side effects. For example, a method of the invention may compare the effects of a test agent on ADRA2a with its effects on other receptors in order to determine whether the test agent is specific.

In an in vivo model as described herein, or an in vitro model such as a cell-based or cell-free assay model as described herein, the effects of a test agent on ADRA2a may be compared with the effects of the same agent on other adrenergic receptors. As discussed above, a preferred ADRA2a antagonist for use in a method of treatment as described herein may be an agent that antagonises ADRA2a, but that does not antagonise other adrenergic receptors. The screening methods of the invention may thus include an additional step of assessing whether the test agent has any effect on the activity or amount of one or more other adrenergic receptors such as one or more adrenergic receptors that are not ADRA2a. In such a method, a test agent may be identified as a suitable ADRA2a antagonist if it is found to decrease the activity or amount of ADRA2a, but not to decrease, not to significantly decrease, not to alter, or not to significantly alter, the activity or amount of one or more other adrenergic receptors in the same assay. A test agent may be identified as a suitable ADRA2a antagonist if it meets any of the requirements discussed above for a selective ADRA2a antagonist of the present invention. For example, a suitable ADRA2a antagonist may not decrease the activity of one or more other adrenergic receptors, or may decrease the activity of other adrenergic receptor(s) to a lesser extent, such as a lower percentage decrease, such as less than 20%, less than 10%, less than 5%, less than 2%, less than 1% or less than 0.5% when compared to its effect on ADRA2a. The one or more other adrenergic receptors may be selected from one or more of alpha 2b, alpha 2c, alpha 1 and beta adrenergic receptors.

Where the assay is carried out in vivo, for example in a rat model of NAFLD or NASH as described herein, such a method may comprise comparing the amount or activity of ADRA2a in the liver or other organs of the test animal in the presence or absence of the test agent. An observation that the level or activity of ADRA2a is decreased in the liver or other organs of animals treated with the test agent suggests that the test agent may be a suitable antagonist of ADRA2a. A further finding that treatment with the same test agent does not significantly decrease or alter the levels or activity of one or more other adrenergic receptors, such as ADRA2b or ADRA2c, may further indicate that the test agent is a suitable specific antagonist of ADRA2a that may be used in the methods of treatment described herein.

In the screening methods described herein, the presence of a lower ADRA2a activity or a decreased amount of ADRA2a in the presence of the test agent indicates that the test agent may be a suitable antagonist of ADRA2a for use in accordance with the present invention to treat an individual having fibrosis in NAFLD.

A test agent that is an antagonist of ADRA2a may result in a decrease in ADRA2a activity (e.g. signalling) or levels of at least 5%, at least 10%, at least 25%, at least 50%, at least 60%, at least 75%, or at least 85% or more in the presence of the test agent compared to in the absence of the test agent. A test agent that is an antagonist of ADRA2a may result in a decrease in ADRA2a activity or levels such that the activity or level of ADRA2a is no longer detectable in the presence of the test agent. Such a decrease may be seen in the sample being tested or, for example where the method is carried out in an animal model, in particular tissue from the animal such as in the liver.

Levels or amounts of ADRA2a may be measured by assessing expression of the ADRA2a gene. Gene expression may be assessed by looking at mRNA production or levels or at protein production or levels. Expression products such as mRNA and proteins may be identified or quantified by methods known in the art. Such methods may utilise hybridisation to specifically identify the mRNA of interest. For example such methods may involve PCR or real-time PCR approaches. Methods to identify or quantify a protein of interest may involve the use of antibodies that bind that protein. For example, such methods may involve immunohistochemistry. Regulation of ADRA2a gene expression may be compared in the presence and absence of a test agent. Thus test agents can be identified that decrease ADRA2a gene expression compared to the level seen in the absence of the test agent. Such test agents may be suitable antagonists of ADRA2a in accordance with the invention.

The effects of a test agent may be assessed by assessing the effects of that agent on a cell that expresses ADRA2a. The specificity of the agent may be assessed in a similar way, by assessing morphometry of the receptor on several cell types which express either only ADRA 2a, or other receptors that are not ADRA2a, such as ADRA2b or ADRA2c, and testing for downstream signals to determine specificity. Such experiments may be carried out using cell types that are known to express the various adrenergic receptor types. Such experiments may be carried out using cells that have been engineered to contain or express one or more adrenergic receptor types, such as ADRA2a that would not naturally be expressed by such cells.

Pharmaceutical Formulations

A suitable ADRA2a antagonist as described herein is typically formulated for administration with a pharmaceutically acceptable carrier or diluent. The antagonist may be any antagonist as defined herein including any antagonist identified by a screening method of the invention. The antagonist may thus be formulated as a medicament with a standard pharmaceutically acceptable carrier(s) and/or excipient(s) as is routine in the pharmaceutical art. The exact nature of the formulation will depend upon several factors including the desired route of administration. Typically, the antagonist may be formulated for oral, intravenous, intragastric, intravascular or intraperitoneal administration.

The pharmaceutical carrier or diluent may be, for example, an isotonic solution such as physiological saline. Solid oral forms may contain, together with the active compound, diluents, e.g. lactose, dextrose, saccharose, cellulose, corn starch or potato starch; lubricants, e.g. silica, talc, stearic acid, magnesium or calcium stearate, and/or polyethylene glycols; binding agents; e.g. starches, gum arabic, gelatin, methylcellulose, carboxymethylcellulose or polyvinyl pyrrolidone; disaggregating agents, e.g. starch, alginic acid, alginates or sodium starch glycolate; effervescing mixtures; dyestuffs; sweeteners; wetting agents, such as lecithin, polysorbates, laurylsulphates; and, in general, non-toxic and pharmacologically inactive substances used in pharmaceutical formulations. Such pharmaceutical preparations may be manufactured in known manner, for example, by means of mixing, granulating, tabletting, sugar-coating, or film-coating processes.

Liquid dispersions for oral administration may be syrups, emulsions or suspensions. The syrups may contain as carriers, for example, saccharose or saccharose with glycerine and/or mannitol and/or sorbitol.

Suspensions and emulsions may contain as carrier, for example a natural gum, agar, sodium alginate, pectin, methylcellulose, carboxymethylcellulose, or polyvinyl alcohol. The suspensions or solutions for intramuscular injections may contain, together with ornithine and at least one of phenylacetate and phenylbutyrate, a pharmaceutically acceptable carrier, e.g. sterile water, olive oil, ethyl oleate, glycols, e.g. propylene glycol, and if desired, a suitable amount of lidocaine hydrochloride.

Where the antagonist to be administered is a nucleic acid molecule, for example where the antagonist is in the form of an expression vector, certain facilitators of nucleic acid uptake and/or expression ("transfection facilitating agents") can also be included in the compositions, for example, facilitators such as bupivacaine, cardiotoxin and sucrose, and transfection facilitating vehicles such as liposomal or lipid preparations that are routinely used to deliver nucleic acid molecules.

A pharmaceutical formulation in accordance with the present invention may further comprise one or more additional therapeutic agents. For example, the formulation may comprise one or more ADRA2a antagonists as defined herein. The formulation may comprise one or more ADRA2a antagonists as described here and also one or more additional therapeutic agents. Preferably the additional therapeutic agent(s) are agents which will assist in the treatment or prophylaxis of the individual to be treated. For example, one or more agents that are effective at treating liver disease may be administered as part of a formulation as described herein. One or more agents that are effective at treating NAFLD or symptom thereof in the patient may be administered as part of a formulation as described herein.

Liposomes may be used to carry the antagonist or formulation of the invention.

Treatment

The present invention provides methods for the treatment of individuals having fibrosis in NAFLD, particularly for the treatment of symptoms and conditions associated with or resulting from fibrosis in NAFLD. Accordingly, the invention provides a method of treating an individual having fibrosis in NAFLD comprising administering to said subject an antagonist of ADRA2a. Similarly, an antagonist of ADRA2a may be provided for use in a method of treating an individual having fibrosis in NAFLD. Also provided is the use of an antagonist of ADRA2a in the manufacture of a medicament for use in the treatment of an individual having fibrosis in NAFLD.

The antagonist may be any antagonist as described herein including any antagonist identified by a screening method of the invention. The antagonist may be provided in a formulation as described herein. An antagonist of ADRA2a as described herein is thus administered to a subject in order to treat fibrosis in NAFLD, or particular symptoms or conditions or features associated with fibrosis in NAFLD in the subject, such as steatosis, cognitive impairment, diabetes mellitus, or progression to NASH.

An antagonist of ADRA2a as described herein can thus be administered to improve the condition of a subject, for example a subject suffering from fibrosis in NAFLD. An antagonist of ADRA2a as described herein may be administered to alleviate the symptoms of a subject, for example the symptoms associated with fibrosis in NAFLD. An antagonist of ADRA2a as described herein may be administered to combat or delay the onset of fibrosis in NAFLD, or NASH, or any symptom associated therewith. The invention can therefore prevent the medical consequences of fibrosis in NAFLD. The individual may be at risk of future acute-on-chronic liver failure (ACLF), for example due to chronic liver disease or progression to cirrhosis. The methods described herein may be used to prevent or delay the onset of liver failure in such a patient, such as a patient progressing to cirrhosis. Use of an antagonist of ADRA2a as described herein may thus extend the life of a patient with fibrosis in NAFLD.

The treatment of fibrosis in NAFLD, or the treatment of an individual having fibrosis in NAFLD as described herein, refers to the treatment of an individual having fibrosis in NAFLD. The individual may be at risk of acute-on-chronic liver failure (ACLF). The methods described herein may be used in the additional prevention or treatment of any such disease.

The individual may be suffering from, or at risk of, one or more symptoms or conditions caused by or associated with fibrosis in NAFLD. Any one or more of these conditions or symptoms may be treated or prevented in accordance with the present invention. For example, the individual may be suffering from, or at risk of, one or more of the following as a result of their fibrosis in NAFLD: steatosis, steatohepatitis, NASH, increased plasma creatinine, renal dysfunction, increased plasma alanine and/or aspartate aminotransferase and cognitive dysfunction. The methods and uses described herein may be of utility in the treatment or prevention of any one or more of these symptoms or conditions in an individual suffering from fibrosis in NAFLD.

As described herein, the antagonist of ADRA2a may lead to decreased expression and/or decreased levels of ADRA2a in the liver of the subject. For example, the antagonist may be an agent that inhibits transcription of ADRA2a in cells of the subject.

As described herein, the antagonist of ADRA2a may lead to decreased activity of ADRA2a in the liver of the individual.

The subject is treated with an antagonist of ADRA2a as described herein. As described above, the antagonist of ADRA2a may be administered alone or in the form of a pharmaceutical formulation. The formulation may comprise one or more antagonists of ADRA2a and may comprise one or more additional therapeutic or prophylactic agents.

Two or more different ADRA2a antagonists as described herein may be used in combination to treat a subject. The two or more antagonists may be administered together, in a single formulation, at the same time, in two or more separate formulations, or separately or sequentially as part of a combined administration regimen.

The ADRA2a antagonist as described herein may be used in combination with a further agent suitable to be used to treat or prevent fibrosis in NAFLD, NASH or fibrotic liver disease. The two or more antagonists may be administered together, in a single formulation, at the same time, in two or more separate formulations, or separately or sequentially as part of a combined administration regimen.

An antagonist or formulation of the invention may be administered by any suitable route. Preferably it is administered by oral, intravenous, intragastric, intraperitoneal or intravascular routes. The antagonist or formulation may be administered directly to the liver of the subject.

The antagonist is administered in a therapeutically effective amount. A suitable dose of an antagonist of the invention can be determined according to various parameters such as the age, weight and condition of the subject to be treated; the type and severity of the liver disease; the route of administration; and the required regimen. A suitable dose can be determined for an individual antagonist. For example, for some antagonists a typical dose may be in the order of from 1 mg/kg/day to 30 g/kg/day. A physician will be able to determine the required dosage of antagonist and for any particular subject.

The present invention is broadly applicable to therapeutic methods and is relevant to the development of prophylactic and/or therapeutic treatments. It is to be appreciated that all references herein to treatment include curative, palliative and prophylactic treatment.

Prophylaxis or therapy includes but is not limited to eliciting an effective decrease in ADRA2a amount, function or activity in order to cause a reduction in one or more symptoms or conditions associated with, or resulting from, fibrosis in NAFLD. The symptoms or conditions may be, for example, any of those discussed above. For example, prophylaxis or therapy may result in: reduced steatosis, improved cognitive ability, reduced risk of diabetes mellitus, improved renal function, decreased plasma creatinine, decreased brain water. Prophylaxis or therapy may result in the prevention or delay of such symptoms or progression to cirrhosis.

Prophylaxis or therapy may have similar effects in relation to any of the symptoms or consequences of fibrosis in NAFLD described herein. That is, treatment in accordance with the present invention may lead to a lessening in the severity of such symptoms or consequences, maintenance of an existing level of such symptoms or consequences or a slowing or reduction in the worsening of such symptoms or consequences.

Patients to be Treated

The present invention relates to the treatment of fibrosis in NAFLD in individuals in need thereof. An individual to be treated in accordance with the present invention may therefore have fibrosis in NAFLD or may be at increased risk of fibrosis in NAFLD or progression to NASH. The subject may have steatosis. The subject may have cognitive impairment. The subject may have diabetes mellitus.

Methods for diagnosing steatosis, NASH, cognitive impairment and diabetes mellitus are well known in the art and in particular to clinicians and veterinarians in the field. Preferably, the subject will have been diagnosed as having steatosis, cognitive impairment and/or diabetes mellitus for example by a medical or veterinarian professional. The subject may display one or more symptoms associated with steatosis, cognitive impairment or diabetes mellitus. Blood sugar levels may be measured as part of a diagnosis of diabetes mellitus.

The individual to be treated may have been diagnosed as suffering from fibrosis in NAFLD, or one or more symptoms or conditions as described herein that may be associated with fibrosis in NAFLD, for example by any of these methods. The individual to be treated may have been diagnosed as being at risk of fibrosis in NAFLD or such symptoms or conditions. For example, the individual may have been diagnosed with one or more symptoms that are associated with fibrosis in NAFLD. The methods described herein may be used to prevent liver failure in a patient having fibrosis in NAFLD.

The subject may be male or female. The subject to be treated may be a human. The subject to be treated may be a non-human animal. The subject to be treated may be a farm animal for example, a cow or bull, sheep, pig, ox, goat or horse or may be a domestic animal such as a dog or cat. The subject may or may not be an animal model for liver disease. The animal may be any age, but will often be a mature adult subject.

EXAMPLES

Methods
Rodent Studies

Sprague Dawley rats (240-300 g) were randomly divided into 3 groups (Standard diet, HFHC+placebo, HFHC+Yohimbine). The animals were kept under controlled temperature ($20\pm2°$ C.) and light (lights on at 08:00-20:00). The standard diet was composed of the following energy sources: 67 g carbohydrates (70 kcal %), 4 g fat (10 kcal %), and 19 g protein (20 kcal %) per 100 g diet. The HFC diet contained 19 g carbohydrates (15 kcal %), 39 g fat (65 kcal %), 2 g cholesterol, and 27 g protein (20 kcal %) per 100 g diet. The study was performed in accordance with local and national guidelines for animal welfare and approved by the institutional Animal Ethics Committee.

Animals were studied after 16 weeks of feeding. Animals in the HFHC group were randomised after 8 weeks of feeding to either treatment with placebo or Yohimbine, in addition to their ongoing diets. Yohimbine Hydrochloride (Product Number Y3125, Sigma-Aldrich, Dorset, UK), an ADRA2A antagonist, was administered in the drinking water at a dosage of 0.4 mg/kg rat/day. In the placebo treated group, an equivalent volume of water was administered. The rats were weighed daily and the Yohimbine treatment weight adjusted.

At the end of 16 weeks of feeding, rats were exsanguinated and the blood and tissues harvested and stored at −80 C for subsequent analyses. Assays performed were as per standard manufacturers recommendations including Cytokines and chemokines (ELISA); ADRA2A (qPCR) and Noradrenaline (HPLC).

Working memory and behavioural testing was through standard psychometric assessments before termination, such as application of the Barnes Maze.

In Vitro Cell Studies
Cell Isolation and Culture

Primary human HSCs (huHSC) were isolated from wedge sections of liver tissue obtained from patients with no history of liver disease undergoing liver resection for colorectal metastasis in the Royal Free Hospital, with local Tissue act for patient benefit ethics approval. All the participants provided written informed consent in accordance with the Helsinki Declaration.

Cells isolation in brief: 10 g of total human liver tissue was digested with 0.01% Collagenase, 0.05% Pronase and 0.001% DNase I without performing perfusion. The homogenate was filtered through a 100 m cell strainer (BD Biosciences) and the flow-through was centrifuged at 50×g for 2 minutes at 4° C. After washing the supernatant, gradient centrifugation was performed at 1400×g for 17 minutes at 4° C. using an 11.5% Optiprep gradient (Sigma-Aldrich Company Ltd.). Finally, the interface was collected and washed. Purity of huHSC was established by detection of CD140b (PDGFRbeta), CD29 (Integrin beta 1) and Cytoglobin B (CYGB). huHSCs were cultured in IMDM supplemented with 20% foetal bovine serum (FBS), Glutamine, 1× nonessential amino acids, 1.0 mM sodium pyruvate, and 1× antibiotic-antimycotic (Life Technologies). Rat primary HSCs cells were cultured in DMEM (high glucose, with sodium pyruvate & glutamax) with 10% FBS (Life Technologies).

Cell Treatments

To determine whether signalling through ADRA2a can lead to modulation of HSC contractility, huHSCs isolated from 3 livers were seeded into serum-free 3D collagen gels. The gels were incubated in serum-free medium (SFM), SFM with 5 uM guanfacine, or SFM with 5 uM guanfacine and SuM BRL44408. Furthermore, to determine whether ADRA2a signalling could also induce HSC contraction in rat liver, rat HSCs were seeded into serum-free 3D collagen gels. They were incubated in SFM or in the presence of 50 uM guanfacine.

Gel Contraction

Human and rat HSCs were cultured within 3D collagen gels (Fibroblast-populated collagen lattices; FPCL). 24 well cell culture plates were pre-coated with sterile 2% BSA (Sigma-Aldrich Company Ltd.) in PBS. Ice-cold neutral collagen solution was made by mixing 1 part 0.2M HEPES pH 8.0 (Life Technologies), 4 parts>2 mg/ml rat tail collagen type I (First Link (UK) Ltd., Wolverhampton, UK), and 5 parts serum-free medium (SFM). For FPCL, equal volumes of the neutral collagen solution and hepatic stellate cells resuspended in SFM or SFM with 5 uM BRL44408 added in. 1 ml of the FPCL was added to each well and allowed to polymerise for ≥2 hours at 37 deg C. 5% $CO_2$. After polymerisation, 1 ml of SFM, SFM with 5 uM guanfacine, SFM with 50 uM guanfacine, or SFM with 5 uM guanfacine and 5uM BRL44408 was added causing detachment of the FPCL from the plate. After 6 hours the contracted gels were imaged using a Fluorchem M imager (ProteinSimple, San Jose CA, USA) with white light transillumination and 607/36 nm filter. Gel areas were measured using ImageJ v1.49 software (US National Institutes of Health, Bethesda MD, USA, http://imagej.nih.gov/ij/).

Example 1

Investigation into the expression of ADRA2α receptors in liver tissue (FIG. 1) found that ADRA2a expression is significantly upregulated in the livers of a rat model of NASH when fed on a high fat, high cholesterol diet, in contrast to control diet fed animals (p=000.34). ADRA2a expression was also upregulated in a further model of inflammatory-fibrotic injury (TAA).

Thus, upregulation of ADRA2a is associated with fatty liver disease and fibrosis progression.

Figure 2:
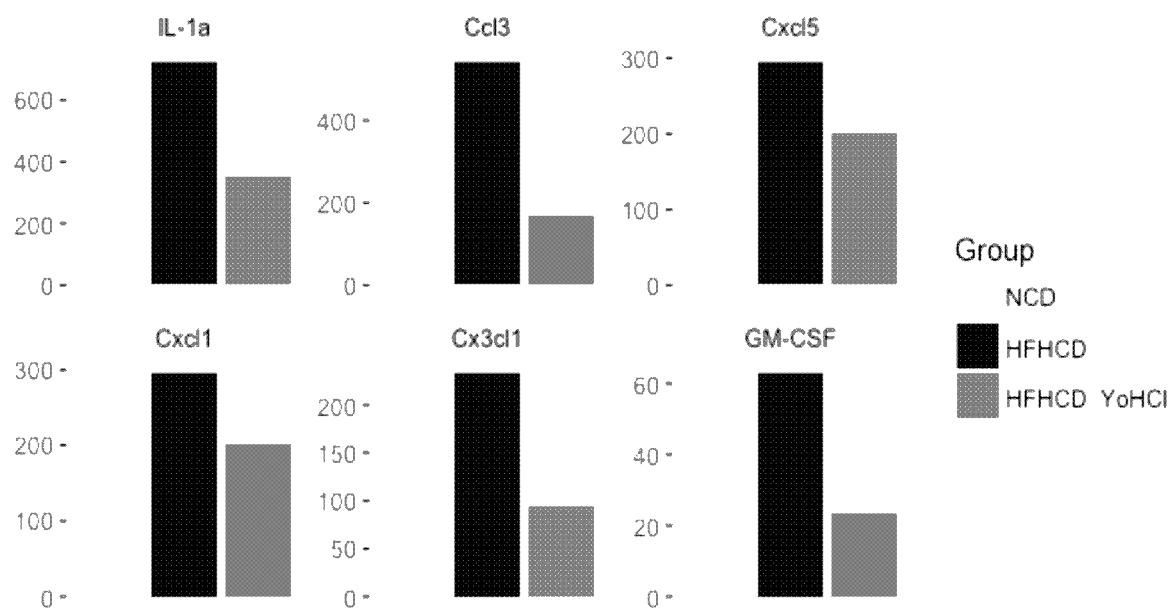
FIG. 2—Increased cytokines and chemokines in a rat model of NASH induced by a high fat high cholesterol (HFHCD) diet fed for 16 weeks compared to standard chow fed control animals (NCD). Treatment with Yohimbine (HFHCD_YoHCl) reduced liver and systemic inflammation. The key cytokines here are largely those that modulate neutrophil chemotaxis and macrophage responses.

It was also found that there was an increase cytokine and chemokine response in a rat model of NASH fed a high fat, high cholesterol diet (HFHC), in comparison to control fed rats (FIG. 2). The key upregulated cytokines are involved in the neutrophil chemotaxis and macrophage activation responses (FIG. 10), associated with a systemic inflammatory response and are modulated by the ADRA2a signalling pathway.

Example 2

Figure 3:
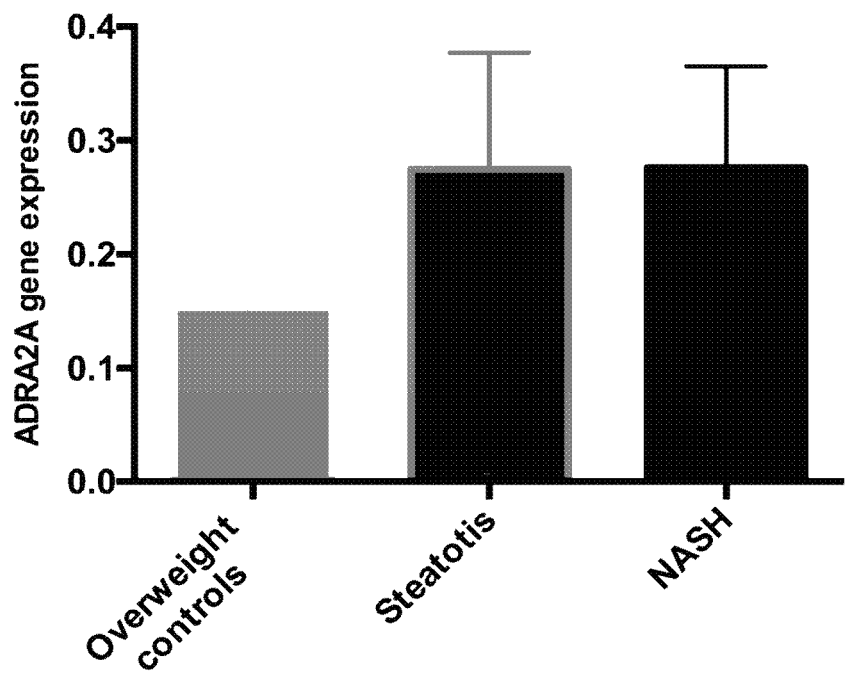
FIG. 3—(A) ADRA2A gene expression in liver tissue is upregulated inpatients with steatosis (n=6) and NASH patients (n=10) compared to overweight controls with no liver disease (n=12). (B) ADRA2A gene expression is more markedly elevated in NAFLD patients with increased fibrosis scores compared to those patients with absence of significant fibrosis.
Figure 3:
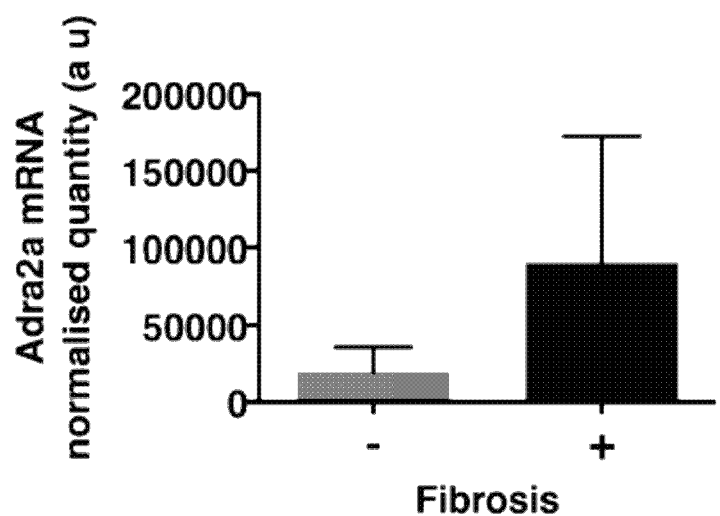
Figure 4:
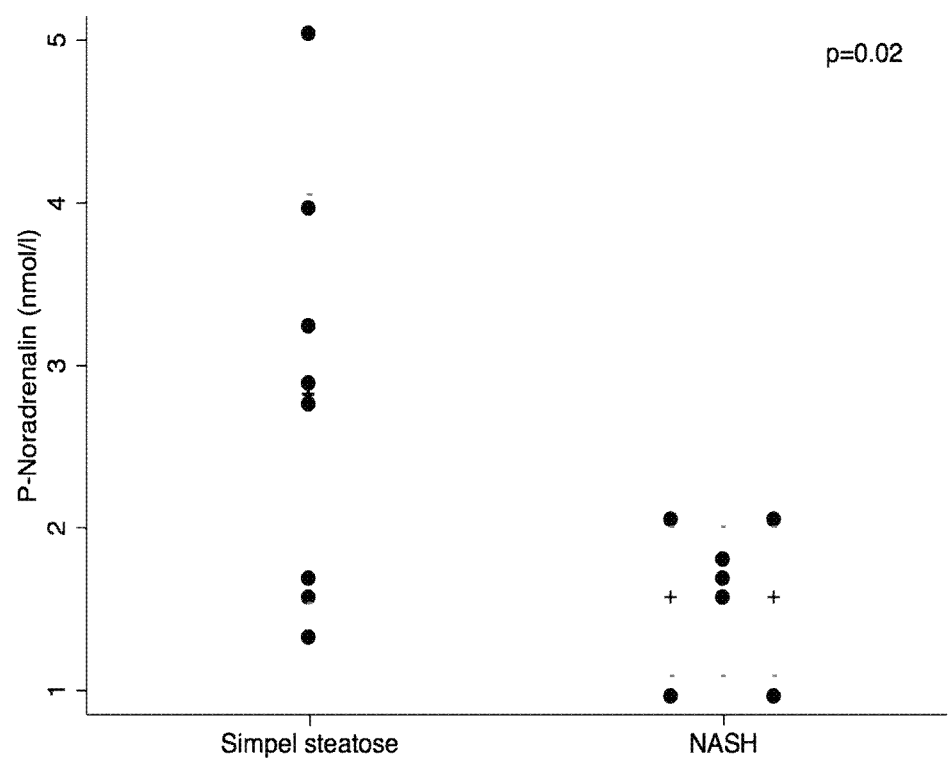
FIG. 4—Plasma noradrenaline levels are significantly reduced in patients with more severe liver disease (NASH) compared to simple steatosis.
Figure 7:
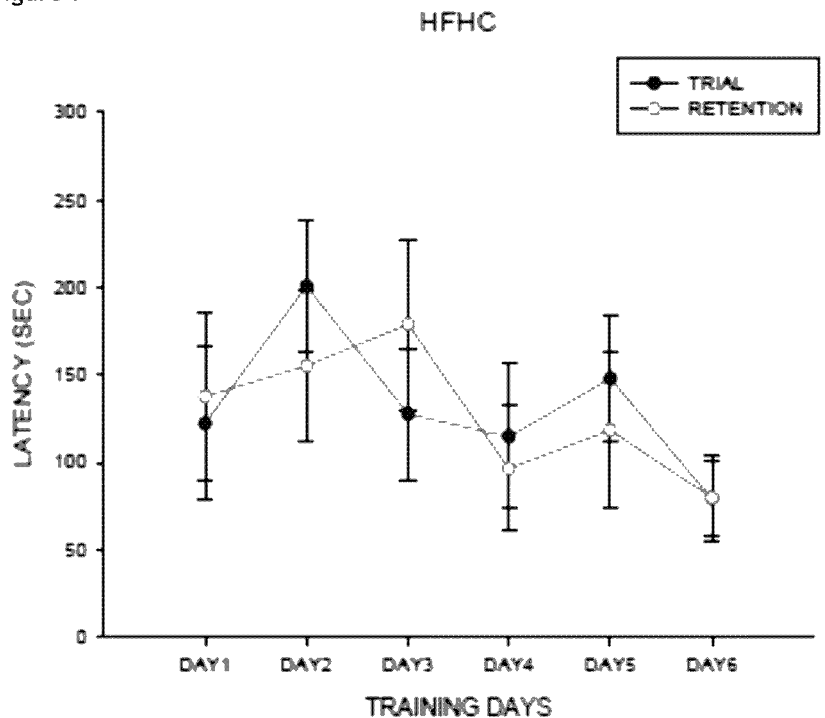
FIG. 7—Working memory test in rats fed a high-fat high-cholesterol (HFHC) diet for 16 weeks to induce NASH with and without treatment with Yohimbine for the last 8 weeks. Yohimbine therapy in NASH rats improves working memory.
Figure 7:
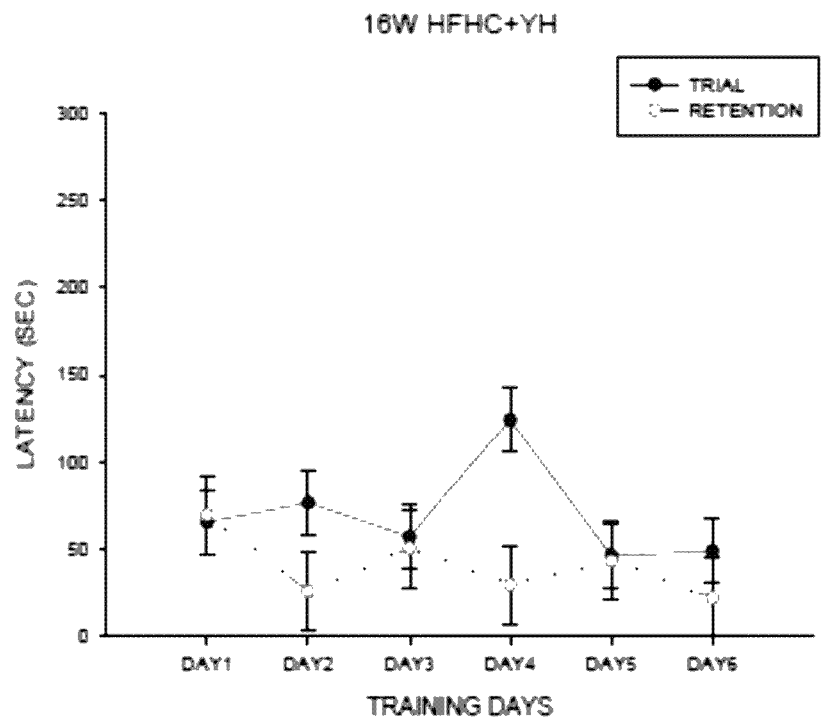

The levels of ADRA2a (FIG. 3) and noradrenaline (FIG. 4) were then investigated in patients with fatty liver disease with either NASH or steatosis. ADRA2A gene expression in liver tissue was upregulated in fatty liver disease patients with steatosis (n=6) and NASH patients (n=10) compared to overweight controls with no evidence of liver disease (n=12) (FIG. 3A). ADRA2A gene expression is also more markedly elevated in NAFLD patients with increased fibrosis scores compared to those patients with absence of significant fibrosis (FIG. 3B). Plasma noradrenaline levels were significantly reduced in patients with more severe liver disease (NASH) compared to simple steatosis. A likely explanation is that an increase in ADRA2a centrally acts to increase feedback inhibition of noradrenaline release from pre-synaptic neurons carrying ADRA2α receptors. However, increased expression of ADRA2a in the brain has potentially deleterious effects on cognitive function such as working memory, as shown in FIG. 7.

Example 3

Figure 5:
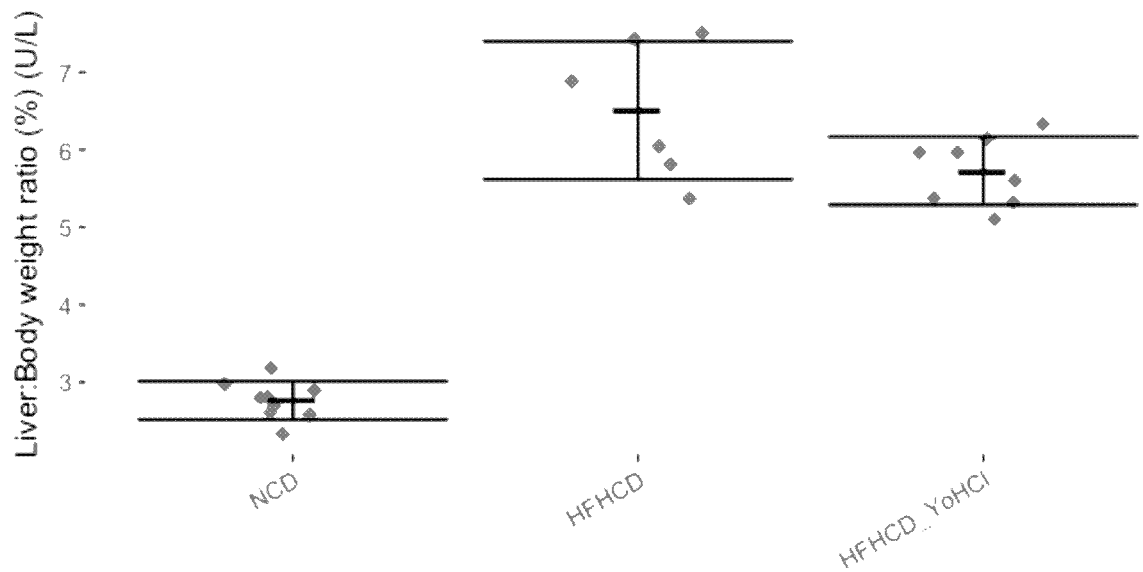
FIG. 5—A). NASH rats fed a HFHC diet for 16 wks have a very fatty liver compared to Normal chow diet (NCD). The Liver-body weight is restored with reduced fat upon treatment with Yohimbine for 8 weeks (HFHCD vs HFHCD_YoHC p=0.014). B). In the HFHC rats, after 8 weeks of Yohimbine therapy, there is a significant reduction in liver injury shown by decreased AST HFHCD vs HFHCD_YoHCl (p=0.007).
Figure 5:
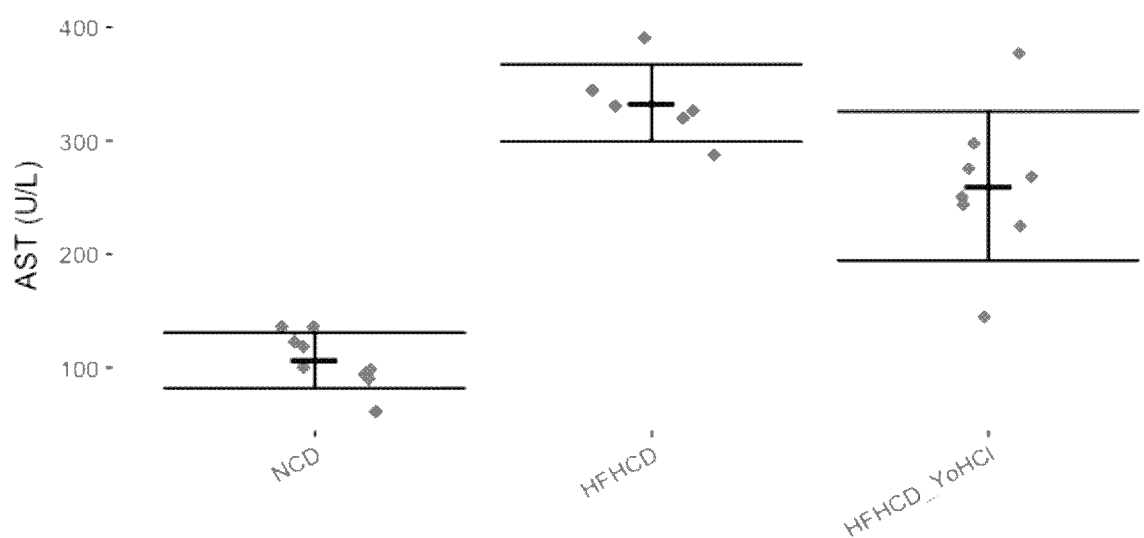

The livers of rat models of NASH were then investigated to determine whether Yohimbine, an ADRA2a antagonist, could provide a therapeutic benefit for fibrosis. NASH rats fed a HFHC diet for 16 wks had a very fatty liver compared to Normal chow diet (NCD). The Liver-body weight ratio was restored with reduced liver fat upon treatment with Yohimbine for 8 weeks (HFHCD vs Control p<0.0001; HFHCD vs HFHCD_YoHCl p=0.014) (FIG. 5a). In the HFHC rats, after 8 weeks of Yohimbine therapy, there was a significant reduction in liver injury shown by decreased AST HFHCD vs HFHCD_YoHC (p=0.007) (FIG. 5b).

Figure 9:
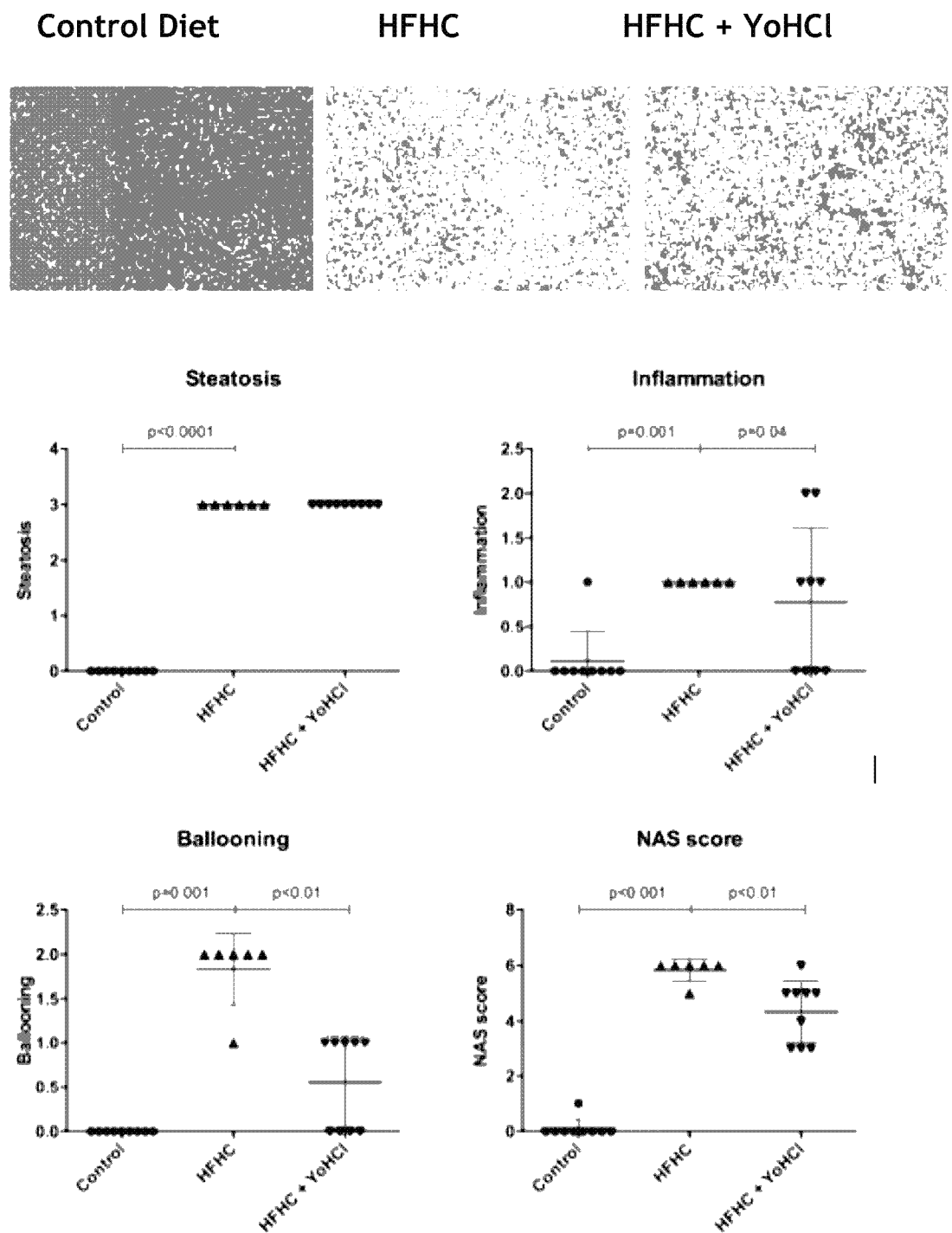
FIG. 9—Representative H&E stain of liver from control rats (upper). Scores of hepatic steatosis, hepatic inflammation, hepatocyte ballooning, and non-alcoholic fatty liver disease (NAFLD) activity score (NAS) in rat models (lower).

Representative Haemotoxylin and Eosin (H&E) stain of liver from control rats, from animals fed a high-fat high-cholesterol (HFHC) diet for 16 weeks and from animals fed a HFHC diet for 8 weeks followed by HFHC diet and Yohimbine hydrochloride for a further 8 weeks (HFHC+YoHCl) (FIG. 9, top panels). Amongst these groups, the 4 graphs shown (FIG. 9, bottom panels) represent the significant increase in hepatic steatosis, hepatic inflammation, hepatocyte ballooning, and non-alcoholic fatty liver disease (NAFLD) activity score (NAS) in HFHC animals (n=6) compared to control diets (n=9), and their significant reduction following treatment for 8 weeks with Yohimbine hydrochloride [HFHC+YoHCl animals (n=9)].

Figure 6:
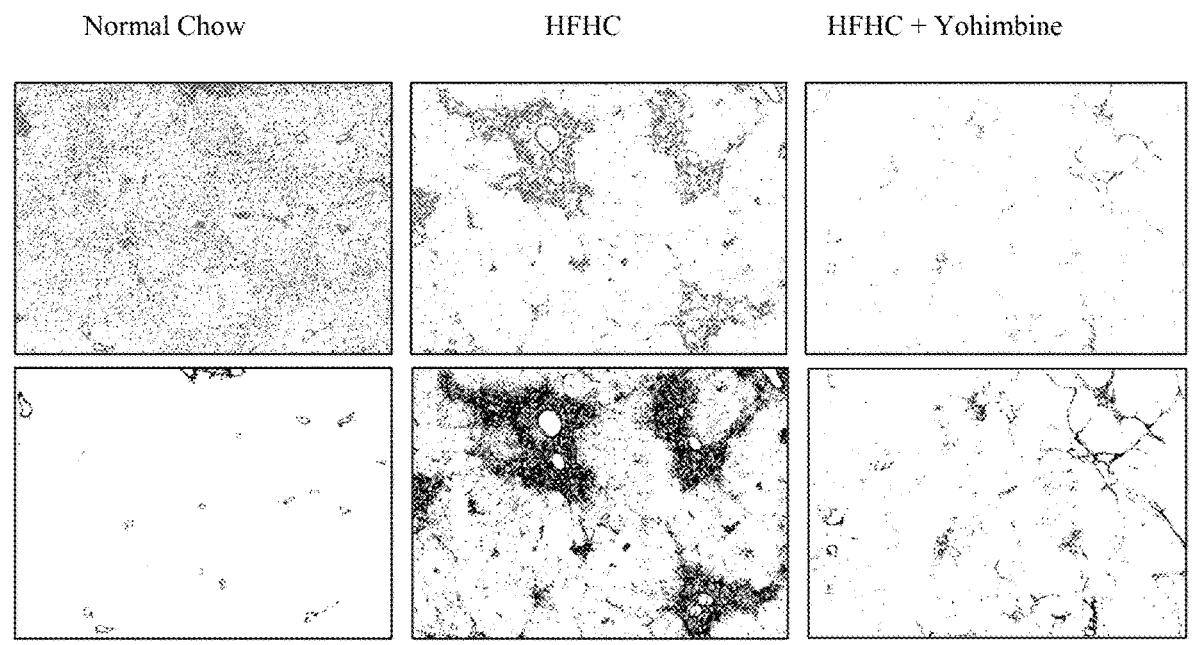
FIG. 6—A). Picro sirius red stained liver (top) and corresponding collagen area quantified (bottom). Graph shows CPA of whole slices of liver from n=6 rats per group. ANOVA p=0.0008; NCD vs HFHCD p=0.0002; HFHCD vs HFHCD_YoHCl p=0.016. B). Genes involved in fibrogenesis (TIMP-1 and Col1a1) are upregulated in the HFHC model (hf) and are significantly (p=0.03 for both) reduced after Yohimbine (hfy) therapy for 8 weeks. MMP2 is also significantly increased in HFHC rats compared to controls, and reduced by therapy with Yohimbine hydrochloride.
Figure 6:
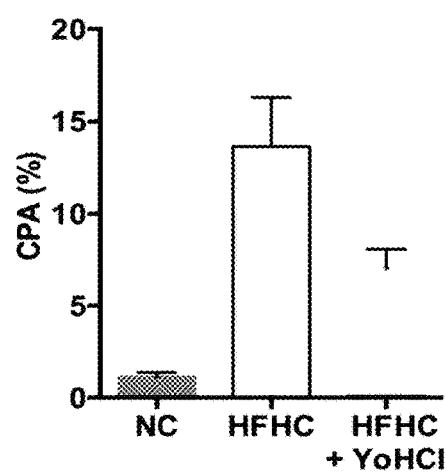
Figure 6:
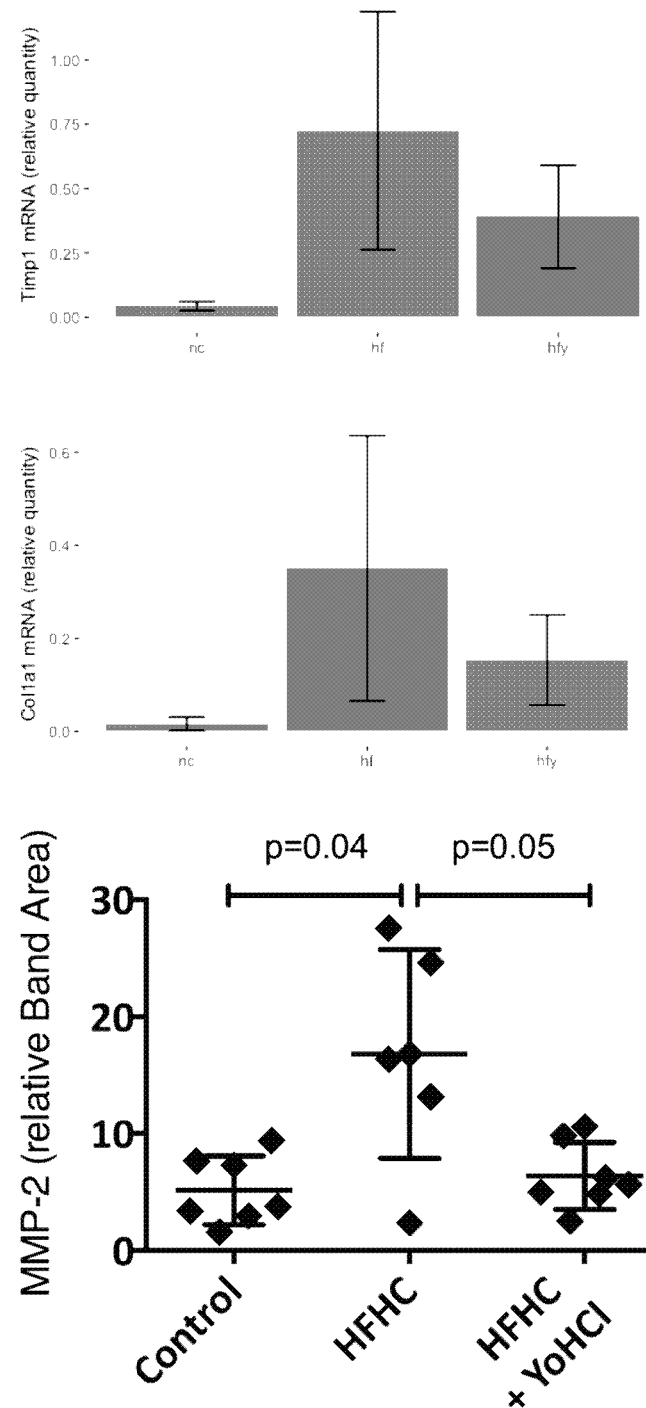

In addition, the Yohimbine treatment group of HFHC diet NASH rats had visually decreased fibrosis (FIG. 6a) and reduced Collagen proportionate area (CPA) in comparison to HFHC NASH rats without treatment. In support of this data, genes involved in fibrogenesis (TIMP-1 and Col1a1) were found to be upregulated in the HFHC model and were significantly (P=0.03 for both) reduced after Yohimbine therapy for 8 weeks (FIG. 6b). Matrix metalloproteinase-2 (MMP2) is involved in the breakdown of extracellular matrix, and is also significantly increased in HFHC rats compared to controls, and reduced by therapy with Yohimbine hydrochloride (FIG. 6B).

Example 4

It was then analysed whether Yohimbine treatment could provide a therapeutic benefit to the cognitive impairment symptom of fibrosis in NAFLD. Working memory test in rats fed a high-fat high-cholesterol (HFHC) diet for 16 weeks to induce NASH, showed significantly impaired working memory compared to control diet fed rats. Following treatment with Yohimbine for the last 8 weeks, NASH rats were found to have significantly improved working memory compared with rats fed a placebo (FIG. 7).

Example 5

A rat model of NASH induced fibrosis by a high fat high cholesterol (HFHC) diet fed for 16 weeks was compared to standard chow fed (control) animals. Some animals were also fed a HFHC diet for 8 weeks followed by HFHC diet and Yohimbine hydrochloride for a further 8 weeks (HFHC+YoHCl)

Figure 8:
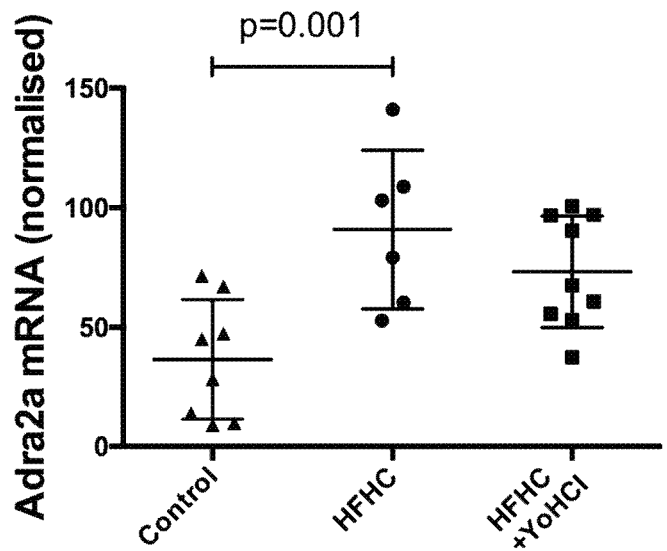
FIG. 8—(A) Expression of ADRA2A receptors in liver tissue is seen to be up-regulated in the NASH rat model; (B) Levels of noradrenaline (Norepinephrine—NE) are markedly increased in the same NASH rat model.
Figure 8:
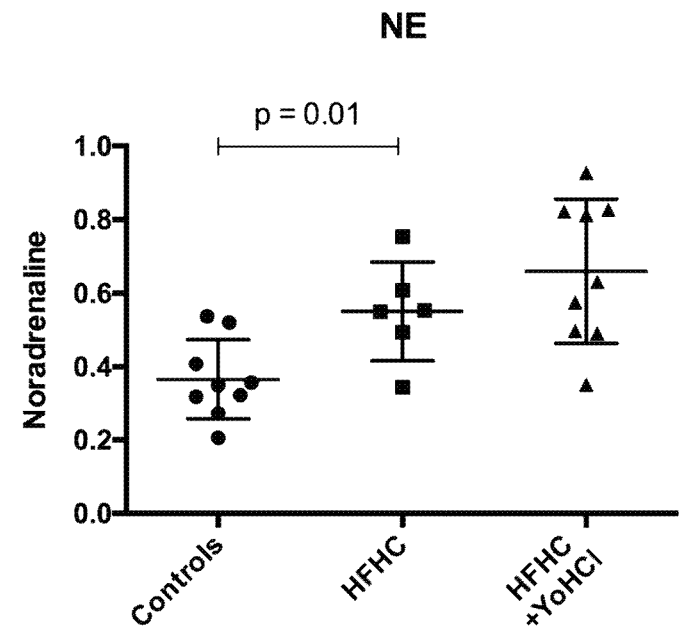

Expression of ADRA2A receptors in liver tissue is seen to be up-regulated in the NASH rat model (FIG. 8A). Treatment with a selective antagonist of ADAR2A, Yohimbine hydrochloride (YoHCl), does not significantly reduce ADRA2A receptor expression. This may be due to the fact that its action is to reduce noradrenaline signalling through the ADRA2A receptor, as discerned by changes in downstream mediators like Phosphorylated ERK1/2.

Levels of noradrenaline (Norepinephrine—NE) are markedly increased in a high fat high cholesterol (HFHC) diet fed NASH fibrosis model compared to control diet rats (FIG. 8B). Treatment with Yohimbine hydrochloride (YoHCl), interestingly causes a further but non-statistical increase in NE levels. This may be due to the blockade of ADRA2A and thereby impact on the additional role of ADAR2A receptors on pre-synaptic sympathetic pathway neurones, impairing the feedback inhibition of further NE release.

Example 6

A rat model of NASH induced fibrosis by a high fat high cholesterol (HFHC) diet fed for 16 weeks was compared to standard chow fed (control) animals. Some animals were also fed a HFHC diet for 8 weeks followed by HFHC diet and Yohimbine hydrochloride for a further 8 weeks (HFHC+ YoHCl).

Figure 10:
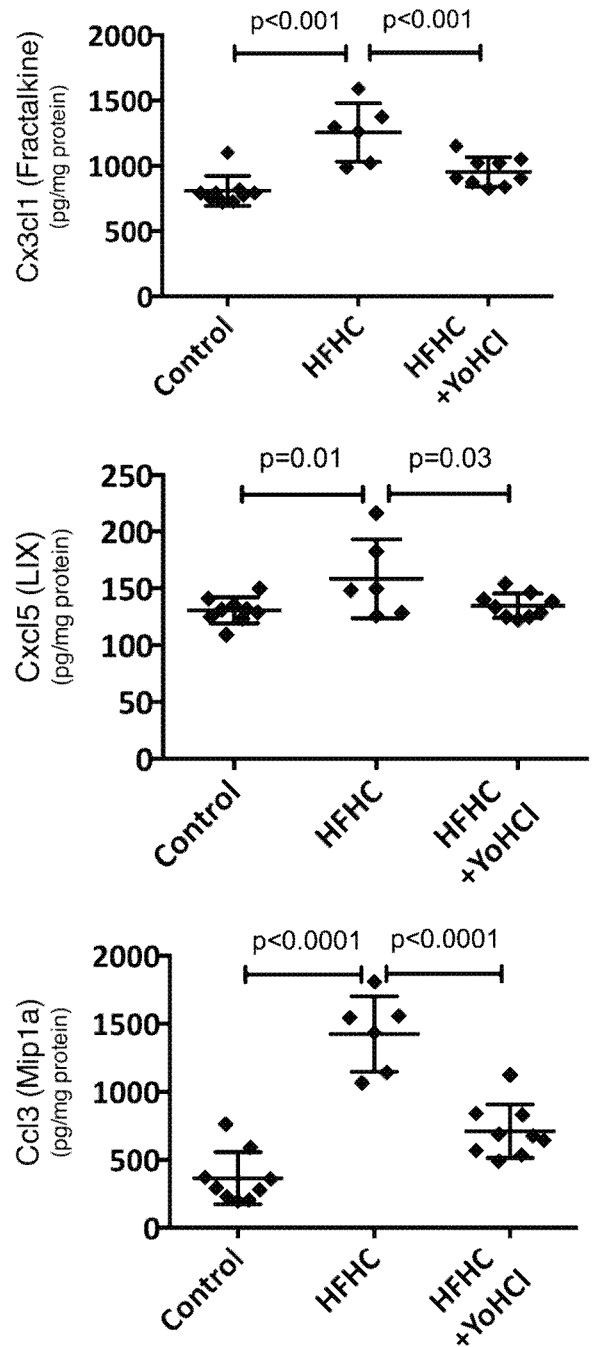
FIG. 10—Protein expression is shown for chemokine (C-X3-C motif) ligand 1 (Cx3CL1), C-X-C motif chemokine 5 (CxCL5), and Chemokine (C-C motif) ligand 3 (CCL3) in control fed rats, in animals fed a high-fat high-cholesterol (HFHC) diet for 16 weeks, and in animals fed a HFHC diet for 8 weeks followed by HFHC diet and Yohimbine hydrochloride for a further 8 weeks (HFHC+YoHCl).

Protein expression is shown for chemokine (C-X3-C motif) ligand 1 (Cx3CL1), C-X-C motif chemokine 5 (CxCL5), and Chemokine (C-C motif) ligand 3 (CCL3) are shown for these groups in FIG. 10. These 3 chemokines are potent chemo-attractants for immune cells, promoting their activation, and linked with fibrosis progression including through activation of stellate cells. All are significantly increased in expression in HFHC fed animals, and decrease markedly after Yohimbine hydrochloride therapy.

Example 7

Figure 11:
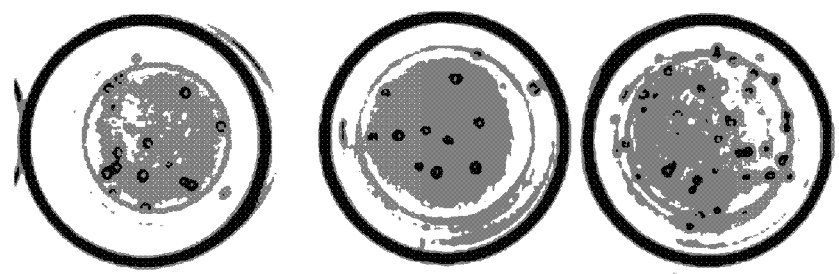
FIG. 11—Primary human hepatic stellate cells were grown in serum free medium, the presence of 5 uM Guanfacine (an ADRA2A agonist), and the presence of both 5 uM Guanfacine and 5uM BRL44408 (a highly specific ADRA2a antagonist) (FIG. 11 from left to right).
Figure 11:
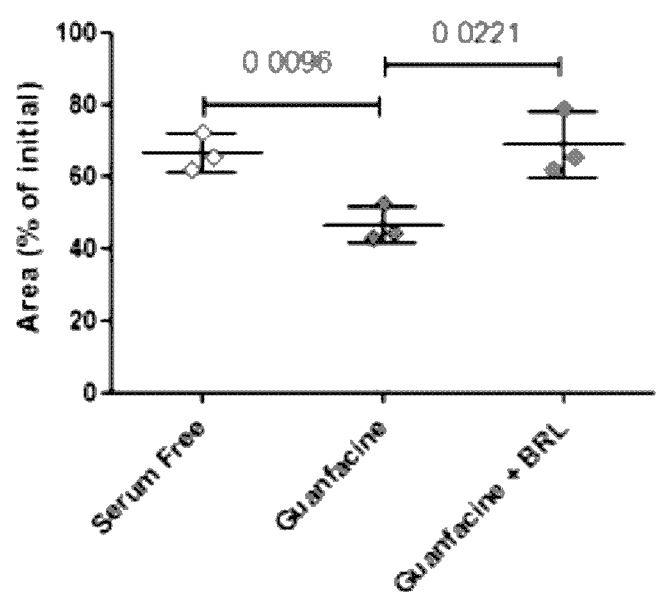

Primary human hepatic stellate cells were grown in serum free medium, the presence of 5 uM Guanfacine (an ADRA2A agonist), and the presence of both 5 uM Guanfacine and 5 uM BRL44408 (FIG. 11, upper panel, from left to right). These show significantly greater contraction in a 3D collagen gel than cells grown in the absence of guanfacine (in serum free medium) (FIG. 11, bottom panel). Cells grown in the presence of both 5 uM Guanfacine and 5 uM BRL44408 (a highly selective ADRA2A antagonist) show less contraction in a 3D collagen gel than cells grown in the presence of guanfacine alone.

The invention claimed is:

1. A method of treating or preventing fibrosis in NAFLD in an individual in need thereof, said method comprising a step of administering to said individual an antagonist of alpha 2a adrenergic receptor (ADRA2a).

2. The method of claim 1, wherein said individual is suffering from non-alcoholic steatohepatitis (NASH).

3. The method of claim 1, wherein the individual is suffering from, or is at risk of one or more of the following, when compared to a subject not suffering from NAFLD: (a) steatosis; (b) steatohepatitis; (c) metabolic syndrome; (d) diabetes mellitus; (e) cognitive dysfunction; (f) functional impairment of daily living; (g) increased plasma alanine and/or aspartate aminotransferases; and/or (h) NASH.

4. The method of claim 1, wherein the individual has a fibrosis stage of 0, 1a, 1b, 1c, 2 or 3.

5. The method of claim 1, wherein administration of the antagonist leads to:
    (a) decreased expression of ADRA2a in the liver of the individual; and/or
    (b) decreased levels of ADRA2a in the liver of the individual; and/or
    (c) decreased activity of ADRA2a in the liver of the individual; and/or
    (d) decreased signalling via ADRA2a in the liver of the individual.

6. The method of claim 1, wherein administration of the antagonist does not lead to:
    (a) increased liver fat; and/or
    (b) increased body weight.

7. The method of claim 1, wherein the antagonist is selected from BRL-44408, BRL-48962, Yohimbine and Rauwolscine.

8. The method of claim 7, wherein the antagonist is Yohimbine.

9. The method of claim 1, wherein the antagonist is a metabolite of Yohimbine, preferably a hydroxylated Yohimbine.

10. The method of claim 1, wherein the antagonist is:
    (a) a specific antagonist of ADRA2a;
    (b) a selective antagonist of ADRA2a;
    (c) not an antagonist of ADRA2b;
    (d) not an antagonist of ADRA2c;
    (e) not an antagonist of ADRA1; and/or
    (f) not an antagonist of ADRB.

* * * * *